(12) United States Patent
Lyons et al.

(10) Patent No.: US 8,114,132 B2
(45) Date of Patent: Feb. 14, 2012

(54) DYNAMIC INTERSPINOUS PROCESS DEVICE

(75) Inventors: Lauren I. Lyons, San Francisco, CA (US); Christopher U. Phan, San Leandro, CA (US)

(73) Assignee: Kyphon Sarl, Neuchatel (CH)

( * ) Notice: Subject to any disclaimer, the term of this patent is extended or adjusted under 35 U.S.C. 154(b) by 197 days.

(21) Appl. No.: 12/687,074

(22) Filed: Jan. 13, 2010

(65) Prior Publication Data

US 2011/0172709 A1   Jul. 14, 2011

(51) Int. Cl.
*A61B 17/70* (2006.01)

(52) U.S. Cl. .......................... 606/249; 606/248

(58) Field of Classification Search .......... 606/246–249; 623/17.11–17.16
See application file for complete search history.

(56) References Cited

U.S. PATENT DOCUMENTS

| | | |
|---|---|---|
| 624,969 A | 5/1899 | Peterson |
| 1,153,797 A | 9/1915 | Kegreisz |
| 1,516,347 A | 11/1924 | Pataky |
| 1,870,942 A | 8/1932 | Beatty |
| 2,077,804 A | 4/1937 | Morrison |
| 2,299,308 A | 10/1942 | Creighton |
| 2,485,531 A | 10/1949 | Dzus et al. |
| 2,607,370 A | 8/1952 | Anderson |
| 2,677,369 A | 5/1954 | Knowles |
| 2,685,877 A | 9/1954 | Dobelle |
| 3,085,659 A | 11/1962 | Eriksson et al. |
| 3,108,595 A | 10/1963 | Overment |
| 3,397,699 A | 8/1968 | Kohl |
| 3,426,364 A | 2/1969 | Lumb |
| 3,648,691 A | 3/1972 | Lumb et al. |
| 3,779,239 A | 12/1973 | Fischer et al. |
| 4,011,602 A | 3/1977 | Rybicki et al. |
| 4,237,875 A | 12/1980 | Termanini |
| 4,257,409 A | 3/1981 | Bacal et al. |
| 4,274,324 A | 6/1981 | Giannuzzi |
| 4,289,123 A | 9/1981 | Dunn |
| 4,327,736 A | 5/1982 | Inoue |
| 4,401,112 A | 8/1983 | Rezaian |
| 4,499,636 A | 2/1985 | Tanaka |
| 4,519,100 A | 5/1985 | Wills et al. |
| 4,553,273 A | 11/1985 | Wu |
| 4,554,914 A | 11/1985 | Kapp et al. |
| 4,573,454 A | 3/1986 | Hoffman |
| 4,592,341 A | 6/1986 | Omagari et al. |

(Continued)

FOREIGN PATENT DOCUMENTS

DE       2821678 A1    11/1979

(Continued)

OTHER PUBLICATIONS

"Dispositivo Intervertebrale Ammortizzante DIAM," date unknown, p. 1.

(Continued)

*Primary Examiner* — Eduardo C. Robert
*Assistant Examiner* — Christina Negrelli

(57) ABSTRACT

Medical devices for the treatment of spinal conditions are described herein. The medical device includes a pair of superior plates with spikes adapted to be embedded in a superior spinous process and a pair of inferior plates with spikes adapted to be embedded in an adjacent inferior spinous process. The superior plates and inferior plates are connected to each other in such a way as to allow relative motion therebetween. A spacer may be disposed between the adjacent spinous processes.

21 Claims, 14 Drawing Sheets

U.S. PATENT DOCUMENTS

| | | |
|---|---|---|
| 4,599,086 A | 7/1986 | Doty |
| 4,604,995 A | 8/1986 | Stephens et al. |
| 4,611,582 A | 9/1986 | Duff |
| 4,632,101 A | 12/1986 | Freedland |
| 4,636,217 A | 1/1987 | Ogilvie et al. |
| 4,646,998 A | 3/1987 | Pate |
| 4,657,550 A | 4/1987 | Daher |
| 4,662,808 A | 5/1987 | Camilleri |
| 4,686,970 A | 8/1987 | Dove et al. |
| 4,704,057 A | 11/1987 | McSherry |
| 4,721,103 A | 1/1988 | Freedland |
| 4,759,769 A | 7/1988 | Hedman et al. |
| 4,787,378 A | 11/1988 | Sodhi |
| 4,822,226 A | 4/1989 | Kennedy |
| 4,827,918 A | 5/1989 | Olerud |
| 4,834,600 A | 5/1989 | Lemke |
| 4,863,476 A | 9/1989 | Shepperd |
| 4,886,405 A | 12/1989 | Blomberg |
| 4,892,545 A | 1/1990 | Day et al. |
| 4,913,144 A | 4/1990 | Del Medico |
| 4,931,055 A | 6/1990 | Bumpus et al. |
| 4,932,975 A | 6/1990 | Main et al. |
| 4,969,887 A | 11/1990 | Sodhi |
| 5,000,166 A | 3/1991 | Karpf |
| 5,011,484 A | 4/1991 | Breard |
| 5,035,712 A | 7/1991 | Hoffman |
| 5,047,055 A | 9/1991 | Bao et al. |
| 5,059,193 A | 10/1991 | Kuslich |
| 5,092,866 A | 3/1992 | Breard et al. |
| 5,098,433 A | 3/1992 | Freedland |
| 5,171,278 A | 12/1992 | Pisharodi |
| 5,201,734 A | 4/1993 | Cozad et al. |
| 5,267,999 A | 12/1993 | Olerud |
| 5,290,312 A | 3/1994 | Kojimoto et al. |
| 5,306,275 A | 4/1994 | Bryan |
| 5,306,310 A | 4/1994 | Siebels |
| 5,312,405 A | 5/1994 | Korotko et al. |
| 5,316,422 A | 5/1994 | Coffman |
| 5,356,423 A | 10/1994 | Tihon et al. |
| 5,360,430 A | 11/1994 | Lin |
| 5,366,455 A | 11/1994 | Dove et al. |
| 5,370,697 A | 12/1994 | Baumgartner |
| 5,390,683 A | 2/1995 | Pisharodi |
| 5,395,370 A | 3/1995 | Muller et al. |
| 5,401,269 A | 3/1995 | Buttner-Janz et al. |
| 5,403,316 A | 4/1995 | Ashman |
| 5,415,661 A | 5/1995 | Holmes |
| 5,437,672 A | 8/1995 | Alleyne |
| 5,437,674 A | 8/1995 | Worcel et al. |
| 5,439,463 A | 8/1995 | Lin |
| 5,454,812 A | 10/1995 | Lin |
| 5,456,689 A | 10/1995 | Kresch et al. |
| 5,458,641 A | 10/1995 | Ramirez Jimenez |
| 5,480,442 A | 1/1996 | Bertagnoli |
| 5,496,318 A | 3/1996 | Howland et al. |
| 5,518,498 A | 5/1996 | Lindenberg et al. |
| 5,540,689 A | 7/1996 | Sanders et al. |
| 5,554,191 A | 9/1996 | Lahille et al. |
| 5,562,662 A | 10/1996 | Brumfield et al. |
| 5,562,735 A | 10/1996 | Margulies |
| 5,571,189 A | 11/1996 | Kuslich |
| 5,571,192 A | 11/1996 | Schonhoffer |
| 5,609,634 A | 3/1997 | Voydeville |
| 5,609,635 A | 3/1997 | Michelson |
| 5,628,756 A | 5/1997 | Barker, Jr. et al. |
| 5,630,816 A | 5/1997 | Kambin |
| 5,645,599 A | 7/1997 | Samani |
| 5,653,762 A | 8/1997 | Pisharodi |
| 5,653,763 A | 8/1997 | Errico et al. |
| 5,658,335 A | 8/1997 | Allen |
| 5,665,122 A | 9/1997 | Kambin |
| 5,674,295 A | 10/1997 | Ray et al. |
| 5,676,702 A | 10/1997 | Ratron |
| 5,685,826 A | 11/1997 | Bonutti |
| 5,690,649 A | 11/1997 | Li |
| 5,693,100 A | 12/1997 | Pisharodi |
| 5,702,391 A | 12/1997 | Lin |
| 5,702,395 A | 12/1997 | Hopf |
| 5,702,452 A | 12/1997 | Argenson et al. |
| 5,702,455 A | 12/1997 | Saggar |
| 5,707,390 A | 1/1998 | Bonutti |
| 5,716,416 A | 2/1998 | Lin |
| 5,723,013 A | 3/1998 | Jeanson et al. |
| 5,725,341 A | 3/1998 | Hofmeister |
| 5,746,762 A | 5/1998 | Bass |
| 5,749,916 A | 5/1998 | Richelsoph |
| 5,755,797 A | 5/1998 | Baumgartner |
| 5,800,547 A | 9/1998 | Schafer et al. |
| 5,810,815 A | 9/1998 | Morales |
| 5,827,289 A | 10/1998 | Reiley et al. |
| 5,836,948 A | 11/1998 | Zucherman et al. |
| 5,849,004 A | 12/1998 | Bramlet |
| 5,860,977 A | 1/1999 | Zucherman et al. |
| 5,888,196 A | 3/1999 | Bonutti |
| 5,941,881 A | 8/1999 | Barnes |
| 5,976,186 A | 11/1999 | Bao et al. |
| 5,980,523 A | 11/1999 | Jackson |
| 6,022,376 A | 2/2000 | Assell et al. |
| 6,048,342 A | 4/2000 | Zucherman et al. |
| 6,068,630 A | 5/2000 | Zucherman et al. |
| 6,074,390 A | 6/2000 | Zucherman et al. |
| 6,102,922 A | 8/2000 | Jakobsson et al. |
| 6,126,689 A | 10/2000 | Brett |
| 6,126,691 A | 10/2000 | Kasra et al. |
| 6,127,597 A | 10/2000 | Beyar et al. |
| 6,132,464 A | 10/2000 | Martin |
| 6,190,413 B1 | 2/2001 | Sutcliffe |
| 6,190,414 B1 | 2/2001 | Young |
| 6,214,037 B1 | 4/2001 | Mitchell et al. |
| 6,214,050 B1 | 4/2001 | Huene |
| 6,235,043 B1 | 5/2001 | Reiley et al. |
| 6,245,107 B1 | 6/2001 | Ferree |
| 6,293,949 B1 | 9/2001 | Justis et al. |
| 6,336,930 B1 | 1/2002 | Stalcup et al. |
| 6,348,053 B1 | 2/2002 | Cachia |
| 6,352,537 B1 | 3/2002 | Strnad |
| 6,364,883 B1 | 4/2002 | Santilli |
| 6,368,350 B1 | 4/2002 | Erickson et al. |
| 6,371,987 B1 | 4/2002 | Weiland et al. |
| 6,375,682 B1 | 4/2002 | Fleischmann et al. |
| 6,402,750 B1 | 6/2002 | Atkinson et al. |
| 6,402,751 B1 | 6/2002 | Hoeck et al. |
| 6,419,703 B1 | 7/2002 | Fallin et al. |
| 6,419,704 B1 | 7/2002 | Ferree |
| 6,432,130 B1 | 8/2002 | Hanson |
| 6,436,140 B1 | 8/2002 | Liu et al. |
| 6,440,169 B1 | 8/2002 | Elberg et al. |
| 6,447,513 B1 | 9/2002 | Griggs |
| 6,447,546 B1 | 9/2002 | Bramlet et al. |
| 6,451,019 B1 | 9/2002 | Zucherman et al. |
| 6,500,178 B2 | 12/2002 | Zucherman et al. |
| 6,511,508 B1 | 1/2003 | Shahinpoor et al. |
| 6,514,256 B2 | 2/2003 | Zucherman et al. |
| 6,520,991 B2 | 2/2003 | Huene |
| 6,527,803 B1 | 3/2003 | Crozet et al. |
| 6,554,833 B2 | 4/2003 | Levy |
| 6,572,653 B1 * | 6/2003 | Simonson ................ 623/17.13 |
| 6,582,433 B2 | 6/2003 | Yun |
| 6,582,467 B1 | 6/2003 | Teitelbaum et al. |
| 6,592,585 B2 | 7/2003 | Lee et al. |
| 6,626,944 B1 | 9/2003 | Taylor |
| 6,645,207 B2 | 11/2003 | Dixon et al. |
| 6,669,729 B2 | 12/2003 | Chin |
| 6,685,742 B1 | 2/2004 | Jackson |
| 6,695,842 B2 | 2/2004 | Zucherman et al. |
| 6,699,246 B2 | 3/2004 | Zucherman et al. |
| 6,709,435 B2 | 3/2004 | Lin |
| 6,723,126 B1 | 4/2004 | Berry |
| 6,730,126 B2 | 5/2004 | Boehm, Jr. et al. |
| 6,733,531 B1 | 5/2004 | Trieu |
| 6,733,534 B2 | 5/2004 | Sherman |
| 6,736,818 B2 | 5/2004 | Perren et al. |
| 6,743,257 B2 | 6/2004 | Castro |
| 6,758,863 B2 | 7/2004 | Estes et al. |
| 6,761,720 B1 | 7/2004 | Senegas |
| 6,770,096 B2 | 8/2004 | Bolger et al. |
| 6,783,530 B1 | 8/2004 | Levy |

| | | |
|---|---|---|
| 6,835,205 B2 | 12/2004 | Atkinson et al. |
| 6,902,580 B2 | 6/2005 | Fallin et al. |
| 6,905,512 B2 | 6/2005 | Paes et al. |
| 6,946,000 B2 | 9/2005 | Senegas et al. |
| 6,981,975 B2 | 1/2006 | Michelson |
| 7,011,685 B2 | 3/2006 | Arnin et al. |
| 7,041,136 B2 | 5/2006 | Goble et al. |
| 7,048,736 B2 | 5/2006 | Robinson et al. |
| 7,070,598 B2 | 7/2006 | Lim et al. |
| 7,081,120 B2 | 7/2006 | Li et al. |
| 7,087,055 B2 | 8/2006 | Lim et al. |
| 7,087,083 B2 | 8/2006 | Pasquet et al. |
| 7,097,648 B1 | 8/2006 | Globerman et al. |
| 7,097,654 B1 | 8/2006 | Freedland |
| 7,101,375 B2 | 9/2006 | Zucherman et al. |
| 7,163,558 B2 | 1/2007 | Senegas et al. |
| 7,201,751 B2 | 4/2007 | Zucherman et al. |
| 7,217,293 B2 | 5/2007 | Branch, Jr. |
| 7,238,204 B2 | 7/2007 | Le Couedic et al. |
| 7,306,628 B2 | 12/2007 | Zucherman et al. |
| 7,335,203 B2 | 2/2008 | Winslow et al. |
| 7,377,942 B2 | 5/2008 | Berry |
| 7,431,735 B2 | 10/2008 | Liu et al. |
| 7,442,208 B2 | 10/2008 | Mathieu et al. |
| 7,445,637 B2 | 11/2008 | Taylor |
| 7,458,981 B2 | 12/2008 | Fielding et al. |
| 7,582,106 B2 | 9/2009 | Teitelbaum et al. |
| 7,604,652 B2 | 10/2009 | Arnin et al. |
| 7,611,316 B2 | 11/2009 | Panasik et al. |
| 7,621,950 B1 | 11/2009 | Globerman et al. |
| 7,641,673 B2 | 1/2010 | Le Couedic et al. |
| 7,658,752 B2 | 2/2010 | Labrom et al. |
| 7,749,252 B2 | 7/2010 | Zucherman et al. |
| 7,771,456 B2 | 8/2010 | Hartmann et al. |
| 7,862,615 B2 | 1/2011 | Carli et al. |
| 7,901,430 B2 | 3/2011 | Matsuura et al. |
| 7,927,354 B2 | 4/2011 | Edidin et al. |
| 2001/0016743 A1 | 8/2001 | Zucherman et al. |
| 2001/0049527 A1 | 12/2001 | Cragg |
| 2002/0143331 A1 | 10/2002 | Zucherman et al. |
| 2003/0040746 A1 | 2/2003 | Mitchell et al. |
| 2003/0045940 A1 | 3/2003 | Eberlein et al. |
| 2003/0065330 A1 | 4/2003 | Zucherman et al. |
| 2003/0153915 A1 | 8/2003 | Nekozuka et al. |
| 2003/0176925 A1 | 9/2003 | Paponneau |
| 2004/0010312 A1 | 1/2004 | Enayati |
| 2004/0010316 A1 | 1/2004 | William et al. |
| 2004/0064094 A1 | 4/2004 | Freyman |
| 2004/0087947 A1 | 5/2004 | Lim et al. |
| 2004/0097931 A1 | 5/2004 | Mitchell |
| 2004/0106995 A1 | 6/2004 | LeCoudic et al. |
| 2004/0117017 A1 | 6/2004 | Pasquet et al. |
| 2004/0133204 A1 | 7/2004 | Davies |
| 2004/0133280 A1 | 7/2004 | Trieu |
| 2004/0158248 A1 | 8/2004 | Ginn |
| 2004/0167625 A1 | 8/2004 | Beyar et al. |
| 2004/0167627 A1 | 8/2004 | Ralph et al. |
| 2004/0172029 A1 | 9/2004 | Lerch |
| 2004/0186577 A1 | 9/2004 | Ferree |
| 2004/0199255 A1 | 10/2004 | Mathieu et al. |
| 2004/0260397 A1 | 12/2004 | Lambrecht et al. |
| 2005/0010293 A1 | 1/2005 | Zucherman et al. |
| 2005/0033434 A1 | 2/2005 | Berry |
| 2005/0049590 A1 | 3/2005 | Alleyne et al. |
| 2005/0049708 A1 | 3/2005 | Atkinson et al. |
| 2005/0056292 A1 | 3/2005 | Cooper |
| 2005/0085814 A1 | 4/2005 | Sherman et al. |
| 2005/0143827 A1 | 6/2005 | Globerman et al. |
| 2005/0165398 A1 | 7/2005 | Reiley |
| 2005/0203512 A1 | 9/2005 | Hawkins et al. |
| 2005/0203519 A1 | 9/2005 | Harms et al. |
| 2005/0203624 A1 | 9/2005 | Serhan et al. |
| 2005/0228391 A1 | 10/2005 | Levy et al. |
| 2005/0245937 A1 | 11/2005 | Winslow |
| 2005/0261768 A1 | 11/2005 | Trieu |
| 2005/0267579 A1 | 12/2005 | Reiley et al. |
| 2005/0273166 A1 | 12/2005 | Sweeney |
| 2005/0288672 A1 | 12/2005 | Ferree |
| 2006/0004447 A1 | 1/2006 | Mastrorio et al. |
| 2006/0004455 A1 | 1/2006 | Leonard et al. |
| 2006/0015181 A1 | 1/2006 | Elberg |
| 2006/0047282 A1 | 3/2006 | Gordon |
| 2006/0064165 A1 | 3/2006 | Zucherman et al. |
| 2006/0084983 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0085069 A1 | 4/2006 | Kim |
| 2006/0085070 A1 | 4/2006 | Kim |
| 2006/0085074 A1 | 4/2006 | Raiszadeh |
| 2006/0089654 A1 | 4/2006 | Lins et al. |
| 2006/0089719 A1 | 4/2006 | Trieu |
| 2006/0095136 A1 | 5/2006 | McLuen |
| 2006/0106381 A1 | 5/2006 | Ferree et al. |
| 2006/0106397 A1 | 5/2006 | Lins |
| 2006/0111728 A1 | 5/2006 | Abdou |
| 2006/0116690 A1 | 6/2006 | Pagano |
| 2006/0122620 A1 | 6/2006 | Kim |
| 2006/0129239 A1 | 6/2006 | Kwak |
| 2006/0136060 A1 | 6/2006 | Taylor |
| 2006/0142858 A1 | 6/2006 | Colleran et al. |
| 2006/0149242 A1 | 7/2006 | Kraus et al. |
| 2006/0182515 A1 | 8/2006 | Panasik et al. |
| 2006/0184247 A1 | 8/2006 | Edidin et al. |
| 2006/0184248 A1 | 8/2006 | Edidin et al. |
| 2006/0195102 A1 | 8/2006 | Malandain |
| 2006/0217726 A1 | 9/2006 | Maxy et al. |
| 2006/0224159 A1 | 10/2006 | Anderson |
| 2006/0224241 A1 | 10/2006 | Butler et al. |
| 2006/0235387 A1 | 10/2006 | Peterman |
| 2006/0235532 A1 | 10/2006 | Meunier et al. |
| 2006/0241601 A1 | 10/2006 | Trautwein et al. |
| 2006/0241613 A1 | 10/2006 | Bruneau et al. |
| 2006/0241643 A1 | 10/2006 | Lim et al. |
| 2006/0241757 A1 | 10/2006 | Anderson |
| 2006/0247623 A1 | 11/2006 | Anderson et al. |
| 2006/0247640 A1 | 11/2006 | Blackwell et al. |
| 2006/0264938 A1 | 11/2006 | Zucherman et al. |
| 2006/0265074 A1* | 11/2006 | Krishna et al. ............. 623/17.15 |
| 2006/0271044 A1 | 11/2006 | Petrini et al. |
| 2006/0271049 A1 | 11/2006 | Zucherman et al. |
| 2006/0271061 A1 | 11/2006 | Beyer et al. |
| 2006/0282075 A1 | 12/2006 | Labrom et al. |
| 2006/0282079 A1 | 12/2006 | Labrom et al. |
| 2006/0293662 A1 | 12/2006 | Boyer, II et al. |
| 2006/0293663 A1 | 12/2006 | Walkenhorst et al. |
| 2007/0005064 A1 | 1/2007 | Anderson et al. |
| 2007/0010813 A1 | 1/2007 | Zucherman et al. |
| 2007/0032790 A1 | 2/2007 | Aschmann et al. |
| 2007/0043362 A1 | 2/2007 | Malandain et al. |
| 2007/0043363 A1 | 2/2007 | Malandain et al. |
| 2007/0049935 A1 | 3/2007 | Edidin et al. |
| 2007/0073289 A1 | 3/2007 | Kwak et al. |
| 2007/0100340 A1 | 5/2007 | Lange et al. |
| 2007/0123861 A1 | 5/2007 | Dewey et al. |
| 2007/0142915 A1 | 6/2007 | Altarac et al. |
| 2007/0151116 A1 | 7/2007 | Malandain |
| 2007/0162000 A1 | 7/2007 | Perkins |
| 2007/0167945 A1 | 7/2007 | Lange et al. |
| 2007/0173822 A1 | 7/2007 | Bruneau et al. |
| 2007/0173823 A1 | 7/2007 | Dewey et al. |
| 2007/0191833 A1 | 8/2007 | Bruneau et al. |
| 2007/0191834 A1 | 8/2007 | Bruneau et al. |
| 2007/0191837 A1 | 8/2007 | Trieu |
| 2007/0191838 A1 | 8/2007 | Bruneau et al. |
| 2007/0198091 A1 | 8/2007 | Boyer et al. |
| 2007/0225807 A1 | 9/2007 | Phan et al. |
| 2007/0225810 A1 | 9/2007 | Colleran et al. |
| 2007/0233068 A1 | 10/2007 | Bruneau et al. |
| 2007/0233074 A1 | 10/2007 | Anderson et al. |
| 2007/0233076 A1 | 10/2007 | Trieu |
| 2007/0233081 A1 | 10/2007 | Pasquet et al. |
| 2007/0233084 A1 | 10/2007 | Betz et al. |
| 2007/0233089 A1 | 10/2007 | DiPoto et al. |
| 2007/0250060 A1 | 10/2007 | Anderson et al. |
| 2007/0270823 A1 | 11/2007 | Trieu et al. |
| 2007/0270824 A1 | 11/2007 | Lim et al. |
| 2007/0270825 A1 | 11/2007 | Carls et al. |

| | | | | | | |
|---|---|---|---|---|---|---|
| 2007/0270826 | A1 | 11/2007 | Trieu et al. | FR | 2700941 A1 | 8/1994 |
| 2007/0270827 | A1 | 11/2007 | Lim et al. | FR | 2703239 A1 | 10/1994 |
| 2007/0270828 | A1 | 11/2007 | Bruneau et al. | FR | 2707864 A1 | 1/1995 |
| 2007/0270829 | A1 | 11/2007 | Carls et al. | FR | 2717675 A1 | 9/1995 |
| 2007/0270834 | A1 | 11/2007 | Bruneau et al. | FR | 2722087 A1 | 1/1996 |
| 2007/0270874 | A1 | 11/2007 | Anderson | FR | 2722088 A1 | 1/1996 |
| 2007/0272259 | A1 | 11/2007 | Allard et al. | FR | 2724554 A1 | 3/1996 |
| 2007/0276368 | A1 | 11/2007 | Trieu et al. | FR | 2725892 A1 | 4/1996 |
| 2007/0276369 | A1 | 11/2007 | Allard et al. | FR | 2730156 A1 | 8/1996 |
| 2007/0276493 | A1 | 11/2007 | Malandain et al. | FR | 2731843 A1 | 9/1996 |
| 2007/0276496 | A1 | 11/2007 | Lange et al. | FR | 2775183 A1 | 8/1999 |
| 2007/0276497 | A1 | 11/2007 | Anderson | FR | 2799948 A1 | 4/2001 |
| 2007/0282443 | A1 | 12/2007 | Globerman et al. | FR | 2816197 A1 | 5/2002 |
| 2008/0021457 | A1 | 1/2008 | Anderson et al. | JP | 02-224660 | 9/1990 |
| 2008/0021460 | A1 | 1/2008 | Bruneau et al. | JP | 09-075381 | 3/1997 |
| 2008/0058934 | A1 | 3/2008 | Malandain et al. | JP | 2003079649 | 3/2003 |
| 2008/0097446 | A1 | 4/2008 | Reiley et al. | SU | 968281 | 1/1983 |
| 2008/0114357 | A1 | 5/2008 | Allard et al. | SU | 1484348 A1 | 6/1989 |
| 2008/0114358 | A1 | 5/2008 | Anderson et al. | WO | WO 94/26192 | 11/1994 |
| 2008/0114456 | A1 | 5/2008 | Dewey et al. | WO | WO 94/26195 | 11/1994 |
| 2008/0147190 | A1 | 6/2008 | Dewey et al. | WO | WO 97/8769 | 5/1997 |
| 2008/0161818 | A1 | 7/2008 | Kloss et al. | WO | WO 98/20939 | 5/1998 |
| 2008/0167685 | A1 | 7/2008 | Allard et al. | WO | WO 99/26562 | 6/1999 |
| 2008/0177306 | A1 | 7/2008 | Lamborne et al. | WO | WO 00/44319 | 8/2000 |
| 2008/0183209 | A1 | 7/2008 | Robinson et al. | WO | WO 01/54598 A1 | 8/2001 |
| 2008/0183211 | A1 | 7/2008 | Lamborne et al. | WO | WO 03/057055 A1 | 7/2003 |
| 2008/0183218 | A1 | 7/2008 | Mueller et al. | WO | WO 2004/047689 A1 | 6/2004 |
| 2008/0195152 | A1 | 8/2008 | Altarac et al. | WO | WO 2004/047691 A1 | 6/2004 |
| 2008/0215094 | A1 | 9/2008 | Taylor | WO | WO 2004/064766 A2 | 10/2004 |
| 2008/0221685 | A9 | 9/2008 | Altarac et al. | WO | WO 2004/084743 A1 | 10/2004 |
| 2008/0234824 | A1 | 9/2008 | Youssef et al. | WO | WO 2004/110300 A2 | 12/2004 |
| 2008/0243250 | A1 | 10/2008 | Seifert et al. | WO | WO 2005/009300 A1 | 2/2005 |
| 2008/0262617 | A1 | 10/2008 | Froehlich et al. | WO | WO 2005/011507 A1 | 2/2005 |
| 2008/0269898 | A1* | 10/2008 | Carls et al. ............ 623/17.11 | WO | WO 2005/044118 A1 | 5/2005 |
| 2008/0281359 | A1 | 11/2008 | Abdou | WO | WO 2005/048856 A1 | 6/2005 |
| 2008/0281360 | A1 | 11/2008 | Vittur et al. | WO | WO 2005/110258 A1 | 11/2005 |
| 2008/0281361 | A1 | 11/2008 | Vittur et al. | WO | WO 2006/064356 A1 | 6/2006 |
| 2009/0054931 | A1 | 2/2009 | Metz-Stavenhagen | WO | WO 2007/034516 A1 | 3/2007 |
| 2009/0062915 | A1 | 3/2009 | Kohm et al. | WO | WO 2007052975 A1 | 5/2007 |
| 2009/0099610 | A1 | 4/2009 | Johnson et al. | WO | WO 2008/132292 A1 | 11/2008 |
| 2009/0105766 | A1 | 4/2009 | Thompson et al. | WO | WO 2009/083276 A1 | 7/2009 |
| 2009/0105773 | A1 | 4/2009 | Lange et al. | WO | WO 2009/083583 A1 | 7/2009 |
| 2009/0234389 | A1 | 9/2009 | Chuang et al. | WO | WO 2009/098536 A1 | 8/2009 |
| 2009/0240283 | A1 | 9/2009 | Carls et al. | | | |
| 2009/0264927 | A1 | 10/2009 | Ginsberg et al. | | | |
| 2009/0270918 | A1 | 10/2009 | Attia et al. | | | |
| 2009/0292314 | A1 | 11/2009 | Mangione et al. | | | |
| 2009/0292316 | A1 | 11/2009 | Hess | | | |
| 2009/0326538 | A1 | 12/2009 | Sennett et al. | | | |
| 2009/0326589 | A1 | 12/2009 | Lemoine et al. | | | |
| 2010/0036419 | A1* | 2/2010 | Patel et al. ............ 606/249 | | | |
| 2010/0121379 | A1 | 5/2010 | Edmond | | | |
| 2010/0191241 | A1 | 7/2010 | McCormack et al. | | | |
| 2010/0204732 | A1 | 8/2010 | Aschmann et al. | | | |
| 2010/0211101 | A1 | 8/2010 | Blackwell et al. | | | |
| 2011/0054531 | A1 | 3/2011 | Lamborne et al. | | | |
| 2011/0144692 | A1* | 6/2011 | Saladin et al. ............ 606/249 | | | |
| 2011/0166600 | A1 | 7/2011 | Lamborne et al. | | | |

FOREIGN PATENT DOCUMENTS

| | | |
|---|---|---|
| DE | 3922044 A1 | 2/1991 |
| DE | 4012622 C1 | 7/1991 |
| DE | 202006018978 U1 | 2/2007 |
| EP | 0322334 B1 | 2/1992 |
| EP | 0767636 B1 | 1/1999 |
| EP | 1004276 A1 | 5/2000 |
| EP | 1011464 B1 | 6/2000 |
| EP | 1138268 A1 | 10/2001 |
| EP | 1148850 B1 | 10/2001 |
| EP | 1148851 B1 | 10/2001 |
| EP | 1302169 A1 | 4/2003 |
| EP | 1330987 A1 | 7/2003 |
| EP | 1552797 A2 | 7/2005 |
| EP | 1854433 A1 | 11/2007 |
| EP | 1905392 A1 | 4/2008 |
| EP | 1982664 A1 | 10/2008 |
| FR | 2623085 A1 | 5/1989 |
| FR | 2625097 A1 | 6/1989 |
| FR | 2681525 A1 | 3/1993 |

OTHER PUBLICATIONS

"Tecnica Operatoria Per II Posizionamento Della Protesi DIAM," date unknown, pp. 1-3.

"Wallis Operative Technique: Surgical Procedure for Treatment of Degenerative Disc Disease (DDD) of Lumbar Spine," date unknown, pp. 1-24, Spine Next, an Abbott Laboratories company, Bordeaux, France.

Benzel et al., "Posterior Cervical Interspinous Compression Wiring and Fusion for Mid to Low Cervical Spinal Injuries," J. Neurosurg., Jun. 1989, pp. 893-899, vol. 70.

Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.

Christie et al., "Dynamic Interspinous Process Technology," SPINE, 2005, pp. S73-S78, vol. 30, No. 16S.

Cousin Biotech, "Analysis of Clinical Experience with a Posterior Shock-Absorbing Implant," date unknown, pp. 2-9.

Cousin Biotech, Dispositif Intervertébral Amortissant, Jun. 1998, pp. 1-4.

Cousin Biotech, Technique Operatoire de la Prothese DIAM, date unknown, Annexe 1, pp. 1-8.

Dickman et al., "The Interspinous Method of Posterior Atlantoaxial Arthrodesis," J. Neurosurg., Feb. 1991, pp. 190-198, vol. 74.

Dubois et al., "Dynamic Neutralization: A New Concept for Restablization of the Spine," Lumbar Segmental Inability, Szpalski et al., eds., 1999, pp. 233-240, Lippincott Williams & Wilkins, Philadelphia, Pennsylvania.

Ebara et al., "Inoperative Measurement of Lumbar Spinal Instability," SPINE, 1992, pp. S44-S50, vol. 17, No. 3S.

Fassio et al., "Treatment of Degenerative Lumbar Spinal Instability L4-L5 by Interspinous Ligamentoplasty," Rachis, Dec. 1991, pp. 465-474, vol. 3, No. 6.

Fassio, "Mise au Point Sur la Ligamentoplastie Inter-Epineuse Lombaire Dans les Instabilites," Maltrise Orthopédique, Jul. 1993, pp. 18, No. 25.

Garner et al., "Development and Preclinical Testing of a New Tension-Band Device for the Spine: the Loop System," Eur. Spine J., Aug. 7, 2002, pp. S186-S191, vol. 11, Suppl. 2.

Guang et al., "Interspinous Process Segmental Instrumentation with Bone-Button-Wire for Correction of Scoliosis," Chinese Medical J., 1990, pp. 721-725, vol. 103.

Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Cong. Neurosurg., Sep. 7-12, 2003, pp. 835-839, Port.

Hambly et al., "Tension Band Wiring-Bone Grafting for Spondylolysis and Spondylolisthesis," SPINE, 1989, pp. 455-460, vol. 14, No. 4.

Kiwerski, "Rehabilitation of Patients with Thoracic Spine Injury Treated by Spring Alloplasty," Int. J. Rehab. Research, 1983, pp. 469-474, vol. 6, No. 4.

Kramer et al., "Intervetertebral Disk Diseases: Causes, Diagnosis, Treatment and Prophylaxis," pp. 244-249, Medical, 1990.

Laudet et al., "Comportement Bio-Mécanique D'Un Ressort Inter-Apophysaire Vertébral Postérieur Analyse Expérimenale Due Comportement Discal En Compression Et En Flexion/Extension," Rachis, 1993, vol. 5, No. 2.

Mah et al., "Threaded K-Wire Spinous Process Fixation of the Axis for Modified Gallie Fusion in Children and Adolescents," J. Pediatric Othopaedics, 1989, pp. 675-679, vol. 9.

Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spinal Surg., 2005, pp. 129-131, vol. 92, Suppl.

McDonnell et al., "Posterior Atlantoaxial Fusion: Indications and Techniques," Techniques in Spinal Fusion and Stabilization, Hitchon et al. eds., 1995, pp. 92-106, Ch. 9, Thieme, New York.

Minns et al., "Preliminary Design and Experimental Studies of a Novel Soft Implant for Correcting Sagittal Plane Instability in the Lumbar Spine," SPINE, 1997, pp. 1819-1825, vol. 22, No. 16.

Müller, "Restauration Dynamique de la Stabilité Rachidienne," Tiré de la Sulzer Technical Review, Jan. 1999, Sulzer Management Ltd, Winterthur, Switzerland.

Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 16.

Petrini et al., "Analisi Di Un'Esperienza Clinica Con Un Implanto Posteriore Ammortizzante," S.O.T.I.M.I. Societe di Ortopedia a Traumatologia dell'Italia Meridionale e Insulare 90 ° Congresso, Jun. 21-23, 2001, Paestum.

Petrini et al., "Stabilizzazione Elastica," Patologia Degenerative del Rachide Lombare, Oct. 5-6, 2001, Rimini.

Porter, "Spinal Stenosis and Neurogenic Claudication," SPINE, Sep. 1, 1996, pp. 2046-2052, vol. 21, No. 17.

Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.

Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.

Richards et al., "The Treatment Mechanism of an Interspinous Process Implant for Lumbar Neurogenic Intermittent Claudication," SPINE, 2005, pp. 744-749, vol. 30, No. 7.

Scarfò, "Instability/Stenosis: Holistic Approach for Less Invasive Surgery," date unknown, University of Siena, Siena, Italy.

Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.

Schlegel et al., "The Role of Distraction in Improving the Space Available in the Lumbar Stenotic Canal and Foramen," SPINE, 1994, pp. 2041-2047, vol. 19, No. 18.

Senegas et al., "Le Recalibrage du Canal Lombaire, Alternative à la Laminectomie dans le Traitement des Sténoses du Canal Lombaire," Revue de Chirurgie Orthopédique, 1988, pp. 15-22.

Senegase et al., "Stabilisation Lombaire Souple," Instabilité Vertébrales Lombaires, Gastambide, ed., 1995, pp. 122-132, Expansion Scientifique Française, Paris, France.

Senegas, "La Ligamentoplastie Inter Vertébrale Lombaire, Alternative a L'Arthrodése," La Revue de Medécine Orthopédique, Jun. 1990, pp. 33-35, No. 20.

Senegas, "La Ligamentoplastie Intervertébrale, Alternative à L'arthrodèse, dans le Traitement des Instabilités Dégénératives," Acta Othopaedica Belgica, 1991, pp. 221-226, vol. 57, Suppl. I.

Senegas, "Mechanical Supplementation by Non-Rigid Fixation in Degenerative Intervertebral Lumbar Segments: the Wallis System," Eur. Spine J., 2002, p. S184-S169, vol. 11, Suppl. 2.

Senegas, "Rencontre," Maîtrise Orthopédique, May 1995, pp. 1-3, No. 44.

Serhan, "Spinal Implants: Past, Present, and Future," 19th International IEEE/EMBS Conference, Oct. 30-Nov. 2, 1997, pp. 2636-2639, Chicago, Illinois.

Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.

Sulzer Innotec, "DIAM—Modified CAD Geometry and Meshing," date unknown.

Taylor et al., "Analyse d'une expérience clinique d'un implant postérieur amortissant," Rachis Revue de Pathologie Vertébrale, Oct./Nov. 1999, vol. 11, No. 4-5, Gieda Inter Rachis.

Taylor et al., "Surgical Requirement for the Posterior Control of the Rotational Centers," date unknown.

Taylor et al., "Technical and Anatomical Considerations for the Placement of a Posterior Interspinous Stabilizer," 2004, pp. 1-10, Medtronic Sofamor Danek USA, Inc., Memphis, Tennessee.

Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.

Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.

Taylor, "Posterior Dynamic Stabilization using the DIAM (Device for Intervertebral Assisted Motion)," date unknown, pp. 1-5.

Taylor, "Présentation à un an d'un dispositif amortissant d'assistance discale," 5èmes journées Avances & Controverses en pathologie rachidienne, Oct. 1-2, 1998, Faculté Libre de Médecine de Lille.

Tsuji et al., "Ceramic Interspinous Block (CISB) Assisted Anterior Interbody Fusion," J. Spinal Disorders, 1990, pp. 77-86, vol. 3, No. 1.

Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.

Voydeville et al., "Experimental Lumbar Instability and Artificial Ligament," Eur. J. Orthop. Surg. Traumatol., Jul. 15, 2000, pp. 167-176, vol. 10.

Voydeville et al., "Lumbar Instability Treated by Intervertebral Ligamentoplasty with Smooth Wedges," Orthopédie Traumatologie, 1992, pp. 259-264, vol. 2, No. 4.

Waldemar Link, "Spinal Surgery: Instrumentation and Implants for Spinal Surgery," 1981, Link America Inc., New Jersey.

Wiltse et al., "The Treatment of Spinal Stenosis," Clinical Orthopaedics and Related Research, Urist, ed., Mar.-Apr. 1976, pp. 83-91, No. 115.

Wisneski et al., "Decompressive Surgery for Lumbar Spinal Stenosis," Seminars in Spine Surgery, Wiesel, ed., Jun. 1994, pp. 116-123, vol. 6, No. 2.

Zdeblick et al., "Two-Point Fixation of the Lumbar Spine Differential Stability in Rotation," SPINE, 1991, pp. S298-S301, vol. 16, No. 6, Supplement.

Zucherman et al., "Clinical Efficacy of Spinal Instrumentation in Lumbar Degenerative Disc Disease," SPINE, Jul. 1992, pp. 834-837, vol. 17, No. 7.

Anasetti et al., "Spine Stability After Implantation of an Interspinous Device: An In Vitro and Finite Element Biomechanical Study," J. Neurosurg. Spine, Nov. 2010, vol. 13, pp. 568-575.

Bellini et al., "Biomechanics of the Lumbar Spine After Dynamic Stabilization," J. Spinal Discord Tech., 2006, vol. 00, No. 00, pp. 1-7.

Buric et al., "DIAM Device for Low Back Pain in Degenerative Disc Disease 24 Months Follow-up," Advances in Minimally Invasive Surgery and Therapy for Spine and Nerves, Alexandre et al., eds., 2011, pp. 177-182, Spinger-Verlat/Wien.

Phillips et al., "Biomechanics of Posterior Dynamic Stabiling Device (DIAM) After Facetectomy and Disectomy," The Spine Journal, 2006, vol. 6, pp. 714-722.

Taylor et al., "Device for Intervertebral Assisted Motion: Technique and Intial Results," 22 Neurosurg. Focus, Jan. 2007, vol. 22, No. 1, pp. 1-6.

Wilke et al., "Biomedical Effect of Different Lumbar Interspinous Implants on Flexibilty and Intradiscal Pressure," Eur Spine J., Vo. 17, published online Jun. 27, 2008, pp. 1049-1056.

Zhao et al., "Efficacy of the Dynamic Interspinous Assisted Motion System in Clinical Treatment of Degenerative Lumbar Disease," Chin. Med. J., 2010, vol. 123, No. 21, pp. 2974-2977.

\* cited by examiner

DYNAMIC INTERSPINOUS PROCESS DEVICE

BACKGROUND

This invention relates generally to the treatment of spinal conditions, and more particularly, to the treatment of spinal stenosis using devices for implantation between adjacent spinous processes.

The clinical syndrome of neurogenic intermittent claudication due to lumbar spinal stenosis is a frequent source of pain in the lower back and extremities, leading to impaired walking, and causing other forms of disability in the elderly. Although the incidence and prevalence of symptomatic lumbar spinal stenosis have not been established, this condition is the most frequent indication of spinal surgery in patients older than 65 years of age.

Lumbar spinal stenosis is a condition of the spine characterized by a narrowing of the lumbar spinal canal. With spinal stenosis, the spinal canal narrows and pinches the spinal cord and nerves, causing pain in the back and legs. It is estimated that approximately 5 in 10,000 people develop lumbar spinal stenosis each year. For patients who seek the aid of a physician for back pain, approximately 12%-15% are diagnosed as having lumbar spinal stenosis.

Common treatments for lumbar spinal stenosis include physical therapy (including changes in posture), medication, and occasionally surgery. Changes in posture and physical therapy may be effective in flexing the spine to decompress and enlarge the space available to the spinal cord and nerves—thus relieving pressure on pinched nerves. Medications such as NSAIDS and other anti-inflammatory medications are often used to alleviate pain, although they are not typically effective at addressing spinal compression, which is the cause of the pain.

Surgical treatments are more aggressive than medication or physical therapy, and in appropriate cases surgery may be the best way to achieve lessening of the symptoms of lumbar spinal stenosis. The principal goal of surgery is to decompress the central spinal canal and the neural foramina, creating more space and eliminating pressure on the spinal nerve roots. The most common surgery for treatment of lumbar spinal stenosis is direct decompression via a laminectomy and partial facetectomy. In this procedure, the patient is given a general anesthesia as an incision is made in the patient to access the spine. The lamina of one or more vertebrae is removed to create more space for the nerves. The intervertebral disc may also be removed, and the adjacent vertebrae may be fused to strengthen the unstable segments. The success rate of decompressive laminectomy has been reported to be in excess of 65%. A significant reduction of the symptoms of lumbar spinal stenosis is also achieved in many of these cases.

Alternatively, the vertebrae can be distracted and an interspinous process device implanted between adjacent spinous processes of the vertebrae to maintain the desired separation between the vertebral segments. Such interspinous process devices typically work for their intended purposes, but some could be improved. Typically the spacer portion of the implant is formed from a hard material. Unfortunately, point loading of the spinous process can occur due to the high concentration of stresses at the point where the hard material of the spacer contacts the spinous process. This may result in excessive subsidence of the spacer into the spinous process. In addition, if the spinous process is osteoporotic, there is a risk that the spinous process could fracture when the spine is in extension. Moreover, some interspinous process devices unduly restrict the patient's freedom of movement.

Thus, a need exists for improvements in interspinous process devices so as to minimize or eliminate point loading of the spinous process and to allow more freedom of movement for the patient.

SUMMARY

An interspinous process device described herein includes a pair of superior plates, a pair of inferior plates, a plurality of spikes located along the interior faces of the superior plates and inferior plates, and a joint that connects the superior plates and the inferior plates and that allows relative movement between the superior plates and inferior plates. In addition, such an interspinous process device may include a spacer disposed between the superior plates and inferior plates. The spacer may be located such that it is adjacent to the mechanism for connecting the superior plates and the inferior plates.

One embodiment of the joint that connects the superior plates and inferior plates is a channel formed in the inferior portion of at least one, but preferably each, of the superior plates that is sized to allow a superior portion of one of the inferior plates to extend into one of the channels. Alternatively, a channel may be formed in the superior portion of at least one, but preferably each, of the inferior plates that is sized to allow an inferior portion of one of the superior plates to extend into one of the channels. The channels preferably extend longitudinally through the inferior portions of the superior plates to allow a linear motion between the superior and inferior plates. Alternatively, the channels may extend in a curvilinear fashion to allow a curvilinear motion between the superior and inferior plates.

Other joints that connect the superior plates and inferior plates are contemplated as well. For example, the inferior portion of the superior plates and the superior portion of the inferior plates may be connected to a universally directional capsule that allows relative movement between the superior plates and the inferior plates in three planes. The capsule can have various characteristics that allow for preferred motion in particular directions. Another mechanism for connecting the superior plates and the inferior plates includes a spring joint. For example, the inferior portion of the superior plates and the superior portion of the inferior plates may be connected to either a compression spring or a torsion spring. The choice of a compression spring or a torsion spring is based on the relative movement desired for the interspinous process device. Yet another mechanism for connecting the superior plates and the inferior plates includes a ball joint. In this embodiment, the inferior portions of the superior plates include a socket and the superior portions of the inferior plates include a ball that fits within the socket of the superior plates. This ball and socket configuration allows relative motion of the superior plates and the inferior plates. Of course, the inferior portions of the superior plates could include the ball and the superior portions of the inferior plates could include the socket.

The interspinous process device described herein is implanted such that one superior plate is located along one side of a superior spinous process and the second superior plate is located along the opposite side of the superior spinous process. The spikes are located on the interior portions of the superior portions of each of the superior plates such that they can be embedded in the superior spinous process to affix the superior plates to the superior spinous process at the desired location. Similarly, one inferior plate is located along one side of an adjacent inferior spinous process and the second inferior plate is located along the opposite side of the adjacent inferior spinous process. Additional spikes are located on the interior portions of the inferior portions of each inferior plate such that they can be embedded in the adjacent inferior spinous process to affix the inferior plates to the inferior spinous process at the desired location.

In this orientation, and with the adjacent vertebrae distracted, the inferior portions of the superior plates and the superior portions of the inferior plates are disposed adjacent to each other to allow desired motion of the adjacent vertebrae but prevent unwanted extension and compression. In one embodiment of the interspinous process device of this invention, the superior portions of the inferior plates are located in channels formed in the inferior portions of the superior plates to allow relative linear motion between the superior and inferior plates. Thus, when the spine is in flexion, the interspinous process device of this invention extends and allows the adjacent spinous processes to move apart as the two adjacent vertebrae pivot. And, when the spine is in extension, the interspinous process device of this invention collapses and allows the adjacent spinous processes to move toward each other as the two adjacent vertebrae pivot in the opposite direction. The height of the channels limits the total distance that the interspinous process device collapses to ensure there is sufficient decompression to eliminate the patient's pain. In addition, a spacer may be included with the interspinous process device to limit the amount of extension by the spine and minimize any stress on the spinous processes caused by the spikes, which are embedded in the spinous processes. Where a universally directional capsule, spring joint or ball and socket joint is used to join the superior and inferior plates, the overall height of the superior plate, inferior plate and capsule, spring joint or ball and socket joint, define the overall minimum spacing between adjacent vertebrae. In the embodiment where a universally directional capsule or spring joint is used, there is some flexion because the capsule and spring joint are somewhat flexible. However extension is limited by the extent of the compressibility of the capsule and spring joint.

DETAILED DESCRIPTION

Figure 1:
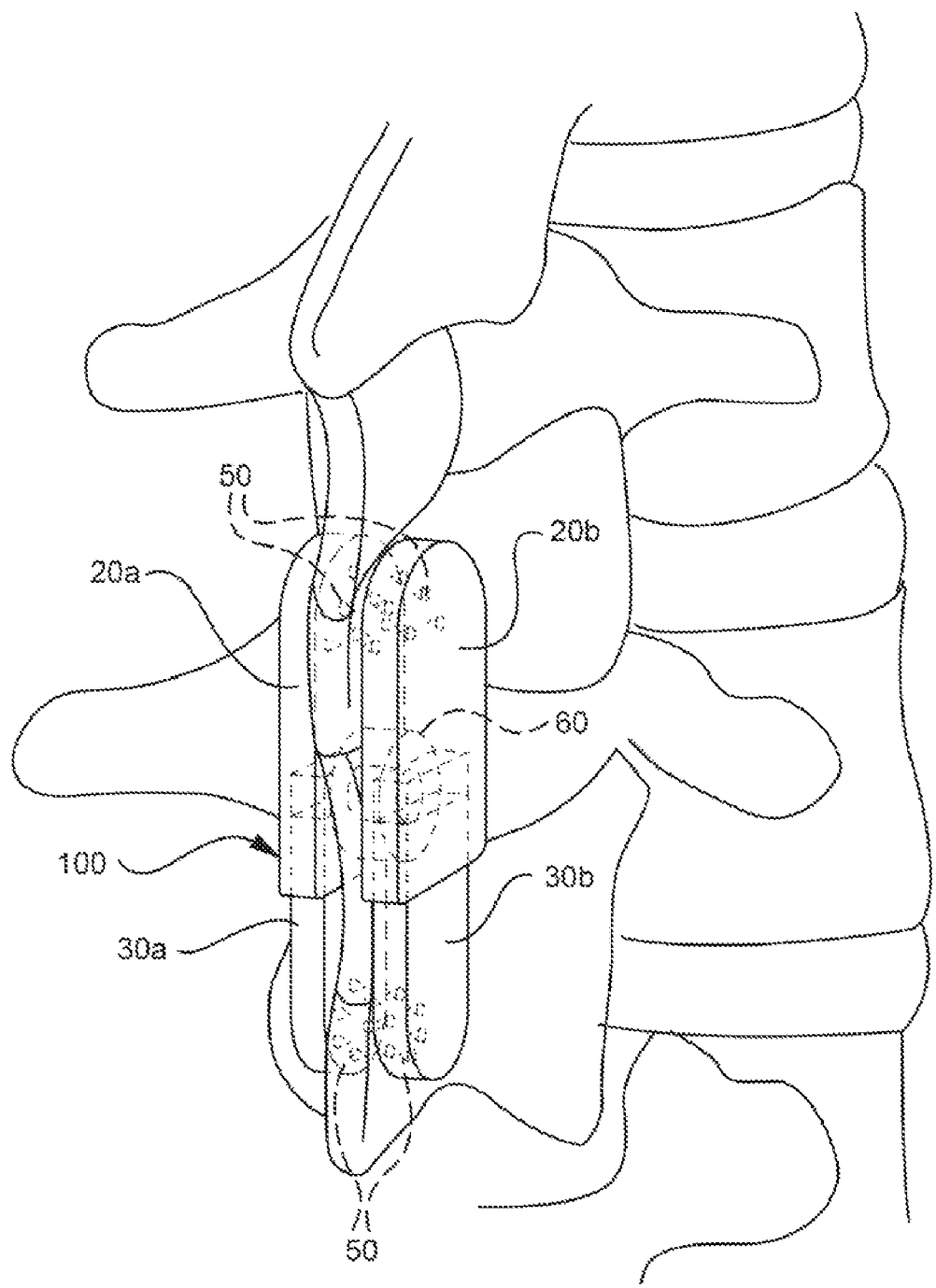
FIG. 1 is a rear perspective view of one embodiment of an interspinous process device and a portion of a spine on which it is located.
Figure 2:
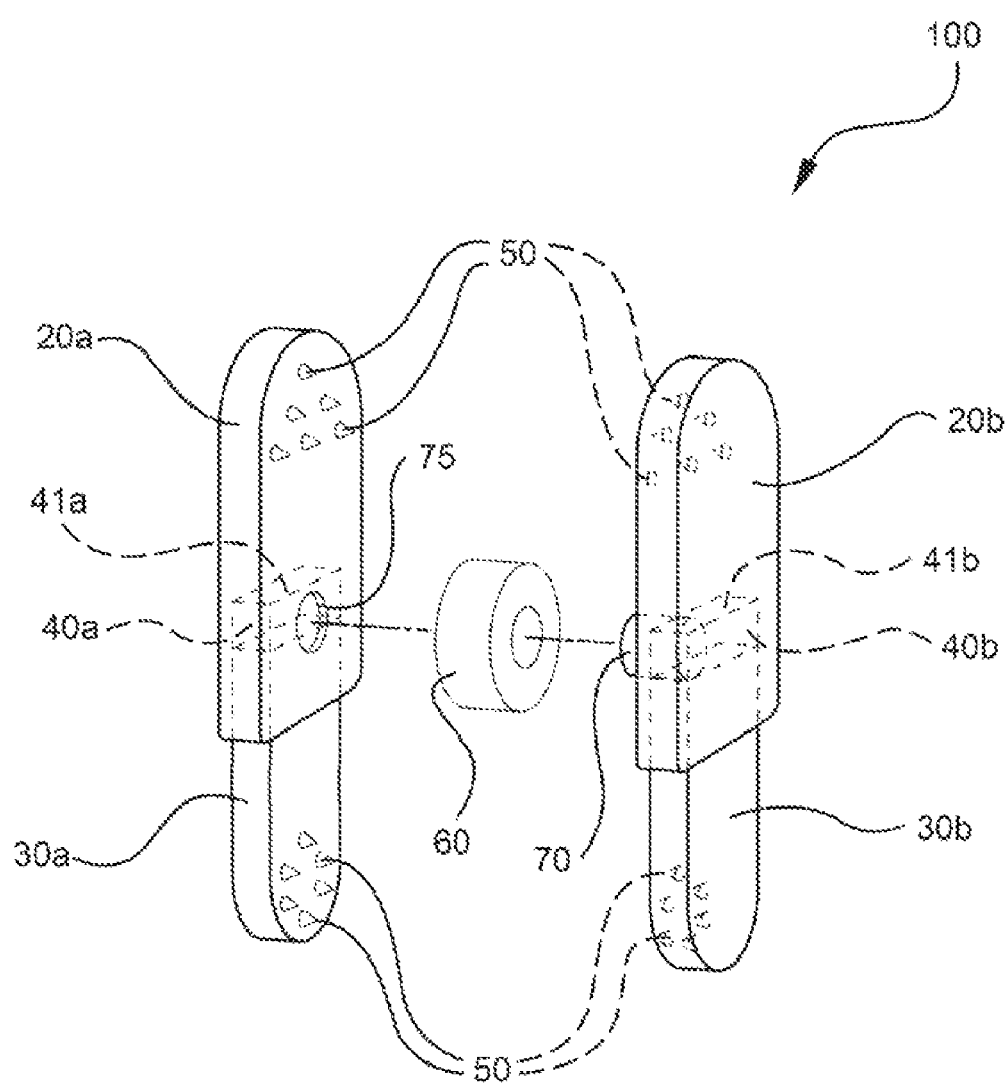
FIG. 2 is a perspective, partially exploded view of the interspinous process device shown in FIG. 1.
Figure 3:
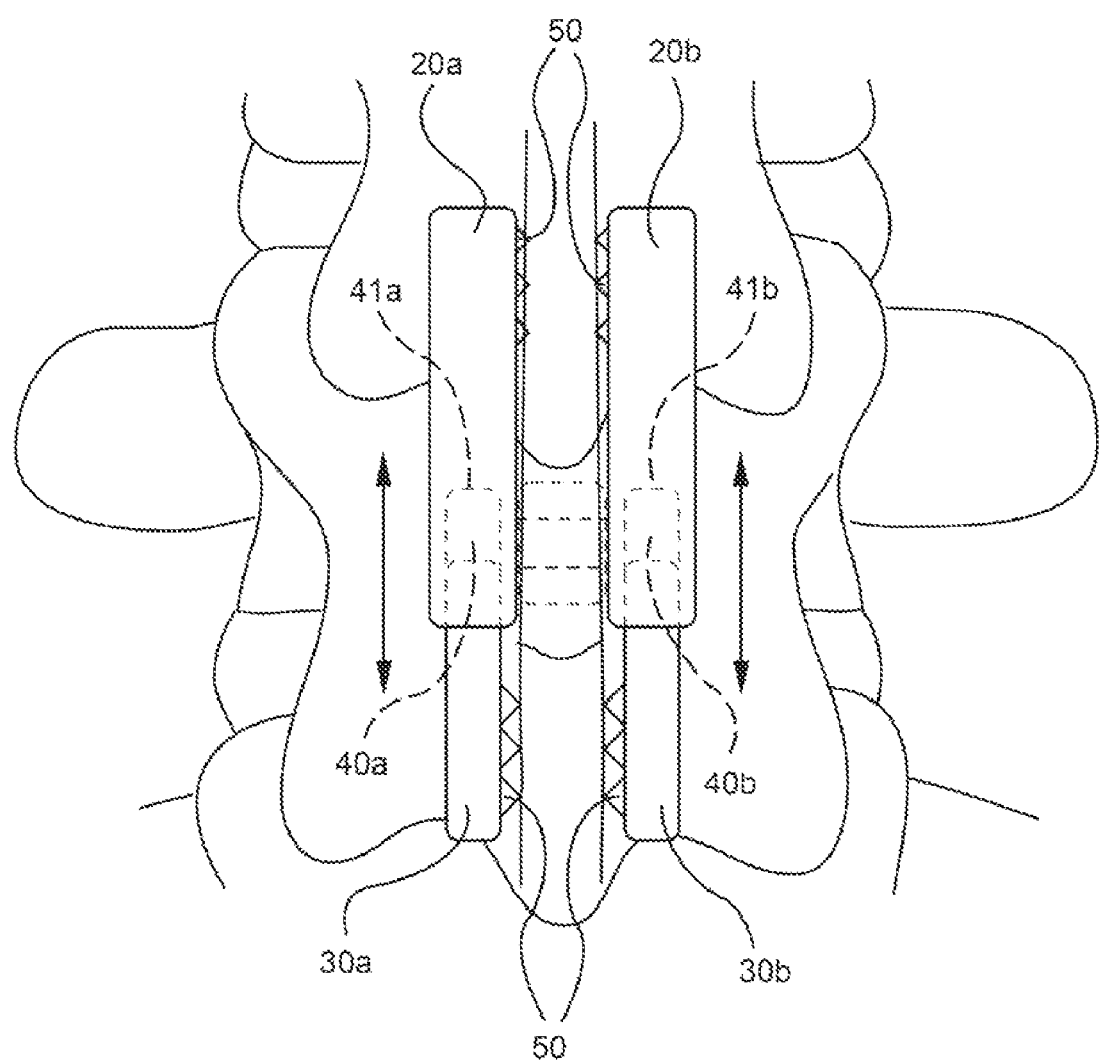
FIG. 3 is a rear elevation view of the interspinous process device shown in FIG. 1 and a portion of a spine on which it is located.
Figure 4:
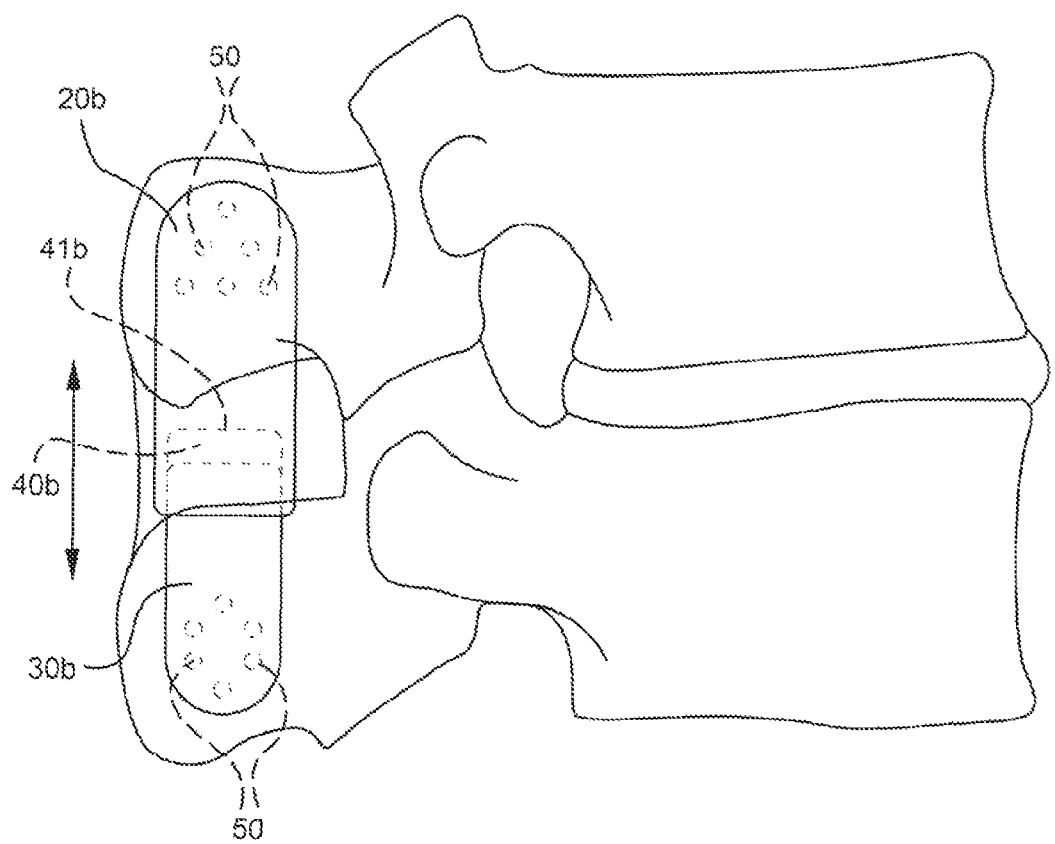
FIG. 4 is a side elevation view of the interspinous process device shown in FIG. 1 and a portion of a spine on which it is located.

As used in this specification and the appended claims, the singular forms "a," "an" and "the" include plural referents unless the context clearly dictates otherwise. Thus, for example, the term "a member" is intended to mean a single member or a combination of members, and "a material" is intended to mean one or more materials, or a combination thereof. Furthermore, the words "proximal" and "distal" refer to directions closer to and away from, respectively, an operator (e.g., surgeon, physician, nurse, technician, etc.) who would insert the medical device into the patient, with the tip-end (i.e., distal end) of the device inserted inside a patient's body first. Thus, for example, the device end first inserted inside the patient's body would be the distal end of the device, while the device end last to enter the patient's body would be the proximal end of the device.

As used in this specification and the appended claims, the term "body" when used in connection with the location where the device of this invention is to be placed to treat lumbar spinal stenosis, or to teach or practice implantation methods for the device, means a mammalian body. For example, a body can be a patient's body, or a cadaver, or a portion of a patient's body or a portion of a cadaver.

As used in this specification and the appended claims, the term "parallel" describes a relationship, given normal manufacturing or measurement or similar tolerances, between two geometric constructions (e.g., two lines, two planes, a line and a plane, two curved surfaces, a line and a curved surface or the like) in which the two geometric constructions are substantially non-intersecting as they extend substantially to infinity. For example, as used herein, a line is said to be parallel to a curved surface when the line and the curved surface do not intersect as they extend to infinity. Similarly, when a planar surface (i.e., a two-dimensional surface) is said to be parallel to a line, every point along the line is spaced apart from the nearest portion of the surface by a substantially equal distance. Two geometric constructions are described herein as being "parallel" or "substantially parallel" to each other when they are nominally parallel to each other, such as for example, when they are parallel to each other within a tolerance. Such tolerances can include, for example, manufacturing tolerances, measurement tolerances or the like.

As used in this specification and the appended claims, the terms "normal", "perpendicular" and "orthogonal" describe a relationship between two geometric constructions (e.g., two lines, two planes, a line and a plane, two curved surfaces, a line and a curved surface or the like) in which the two geometric constructions intersect at an angle of approximately 90 degrees within at least one plane. For example, as used herein, a line is said to be normal, perpendicular or orthogonal to a curved surface when the line and the curved surface intersect at an angle of approximately 90 degrees within a plane. Two geometric constructions are described herein as being "normal", "perpendicular", "orthogonal" or "substantially normal", "substantially perpendicular", "substantially orthogonal" to each other when they are nominally 90 degrees to each other, such as for example, when they are 90 degrees to each other within a tolerance. Such tolerances can include, for example, manufacturing tolerances, measurement tolerances or the like.

Interspinous process device 100 includes a pair of superior plates 20a and 20b, a pair of inferior plates 30a and 30b, a plurality of spikes 50 located along the interior faces of superior plates 20a, 20b and inferior plates 30a, 30b, and a joint that connects superior plates 20a, 20b and inferior plates 30a, 30b and that allows relative movement between superior plates 20a, 20b and inferior plates 30a, 30b. Superior plate 20a is connected to superior plate 20b by a connecting rod 70, which may be formed on one of the superior plates. The other end of connecting rod 70 fits in a recess or hole 75 formed in the other superior plate. Alternatively, the connecting rod could be a separate piece that fits into recesses formed in each of superior plates 20a and 20b or inferior plates 30a, 30b. In addition, interspinous process device 100 may include a spacer 60 disposed between superior plates 20a, 20b and/or inferior plates 30a, 30b adjacent to the joint that connects superior plates 20a, 20b and inferior plates 30a, 30b. Spacer 60 is preferably disposed about connecting rod 70. It is to be understood that this general configuration may be used with all of the various joint mechanisms that are described herein for joining the superior plates to the inferior plates.

Figure 5:
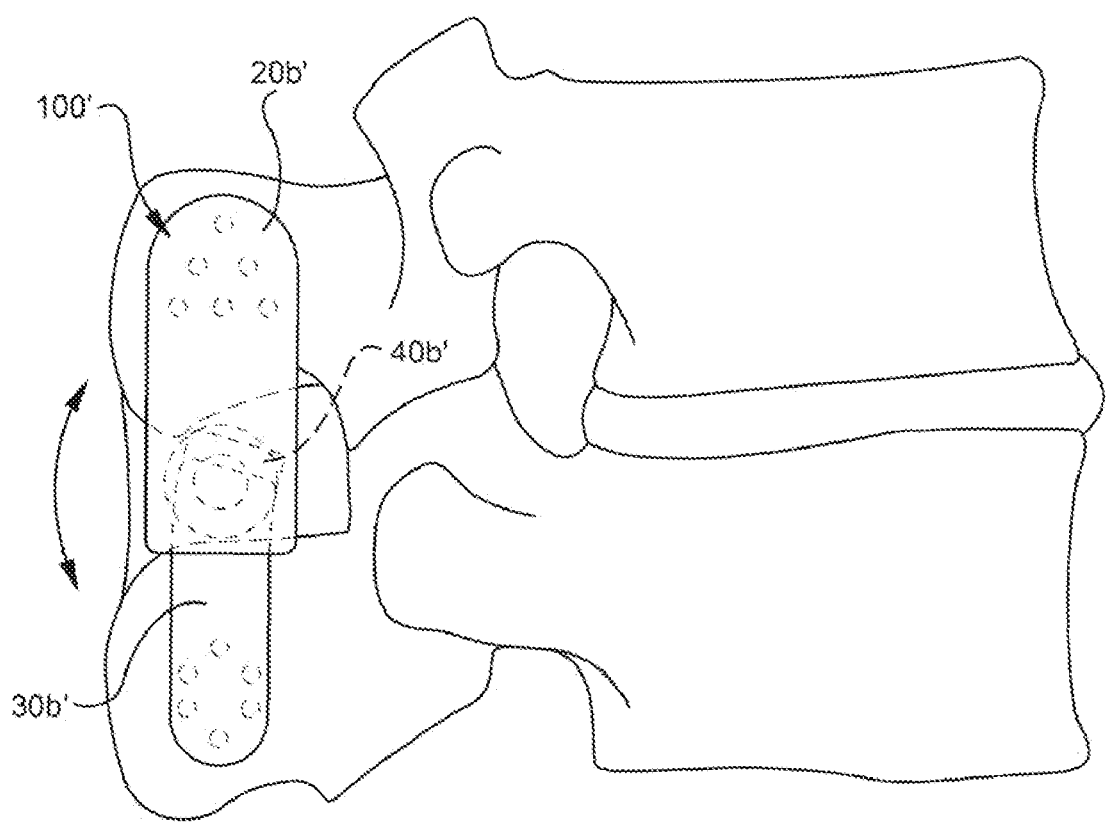
FIG. 5 is a side elevation view of another embodiment of an interspinous process device and a portion of a spine on which it is located.
Figure 6:
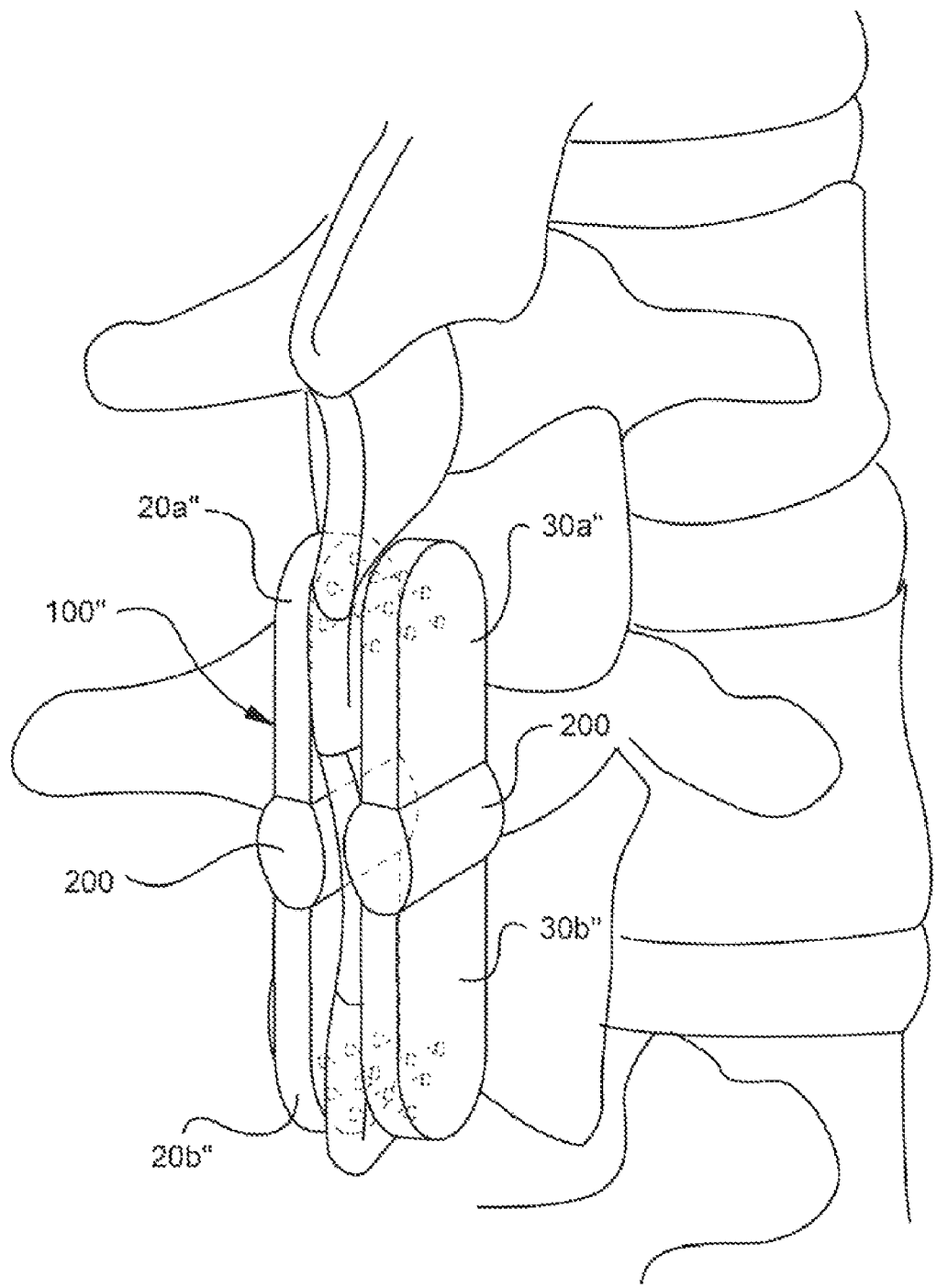
FIG. 6 is a rear perspective view of another embodiment of an interspinous process device and a portion of a spine on which it is located.
Figure 7:
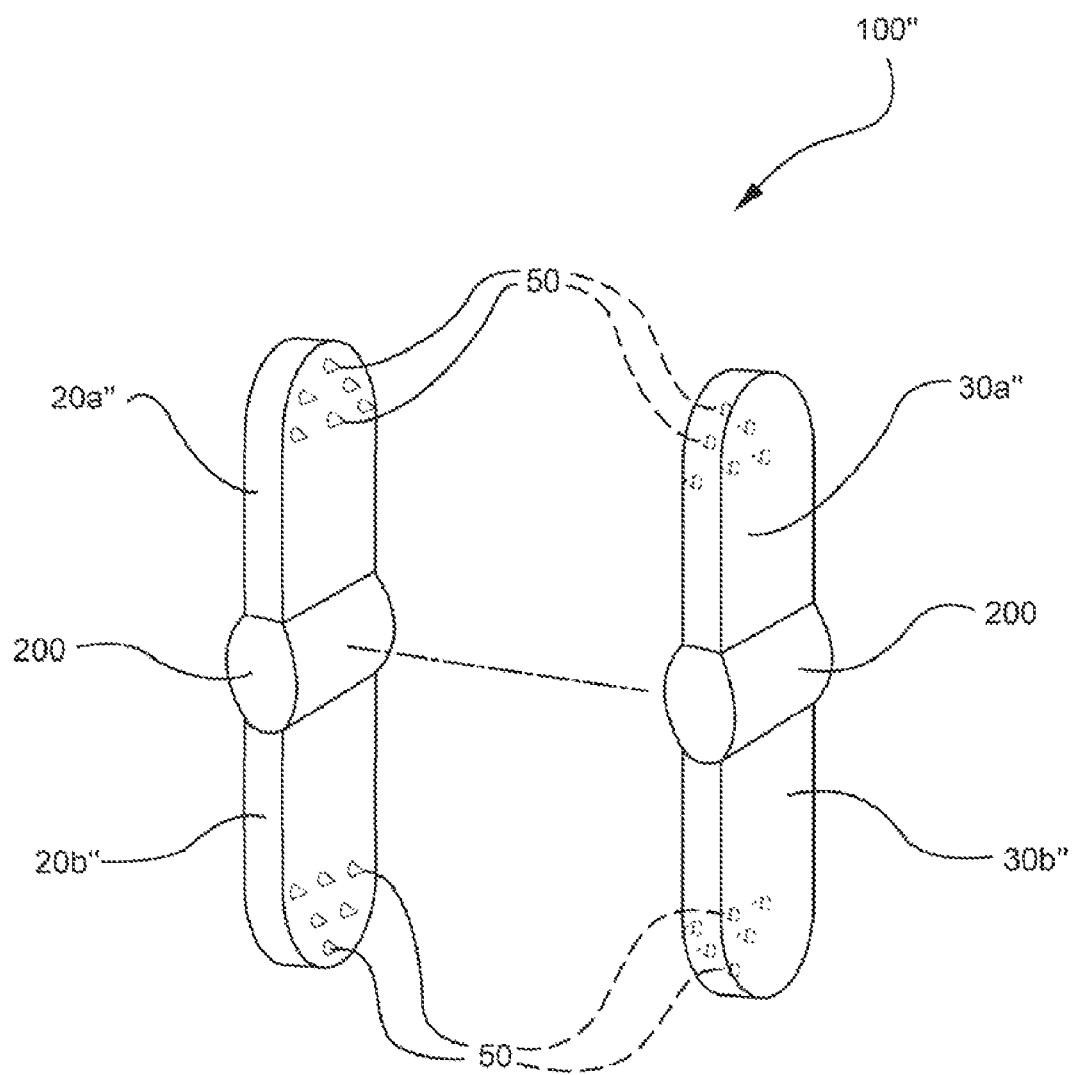
FIG. 7 is a perspective, partially exploded view of the embodiment of the interspinous process device shown in FIG. 6.
Figure 8:
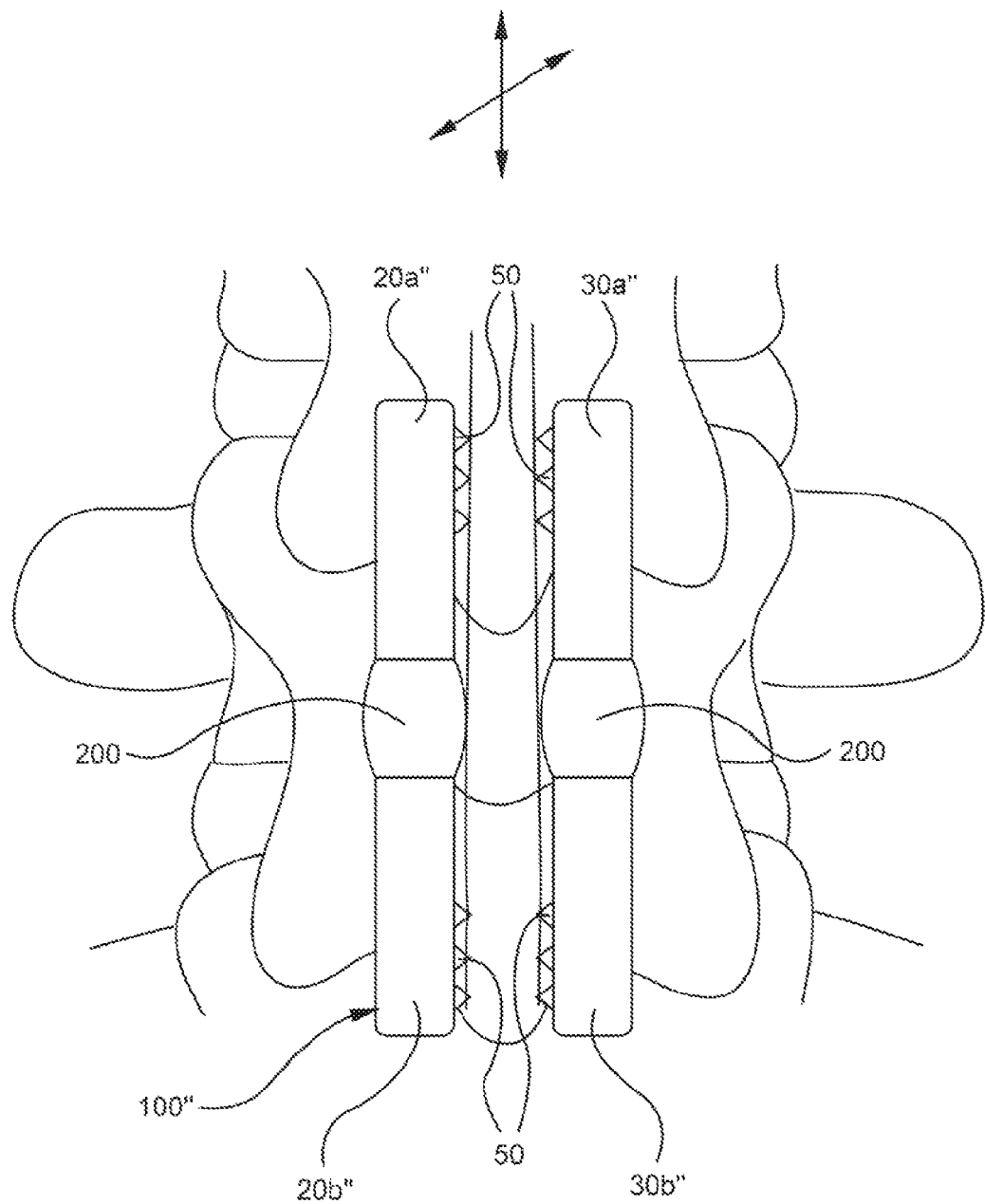
FIG. 8 is a rear elevation view of the embodiment of the interspinous process device shown in FIG. 6 and a portion of a spine on which it is located.
Figure 9:
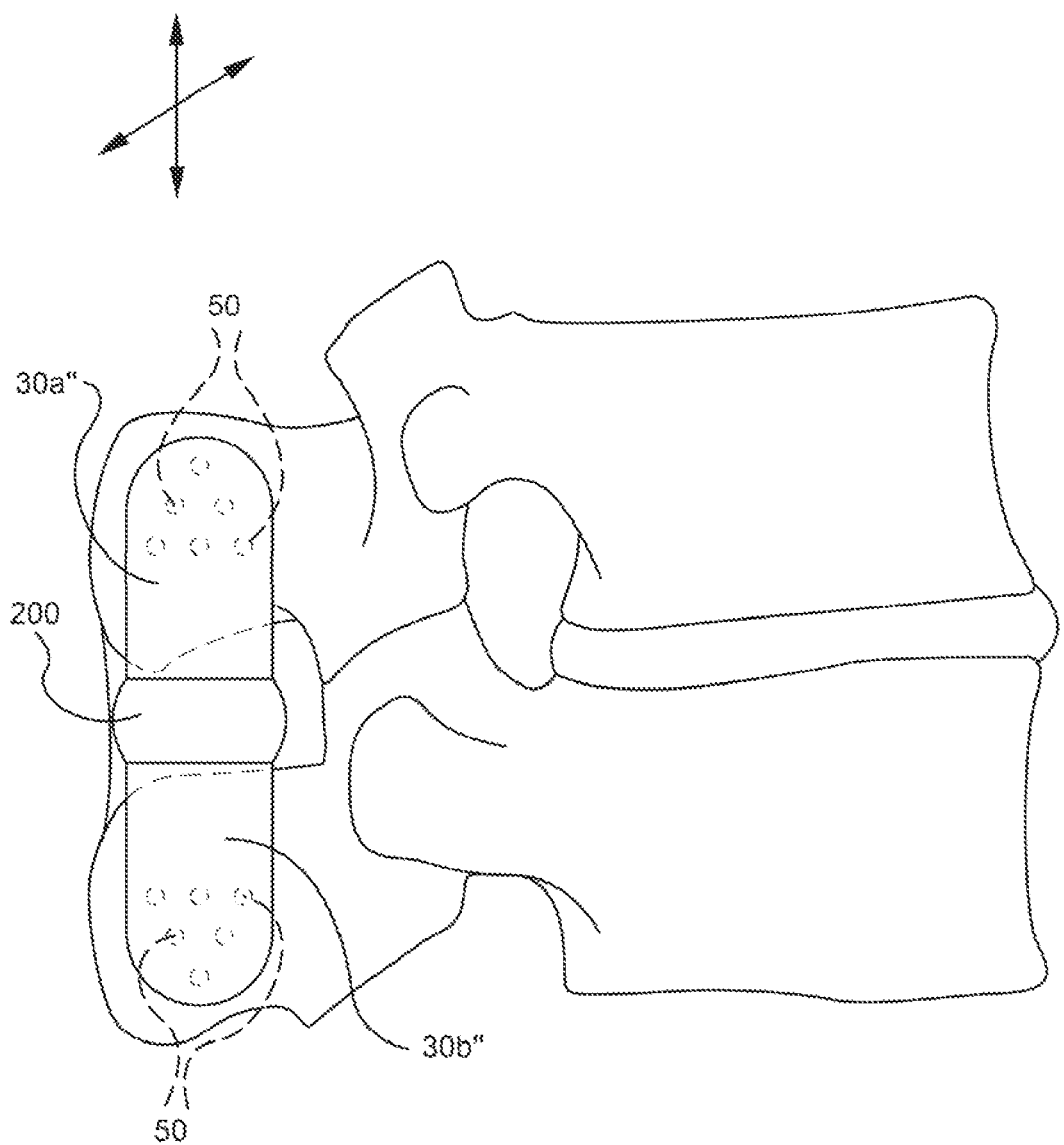
FIG. 9 is a side elevation view of the embodiment of the interspinous process device shown in FIG. 6 and a portion of a spine on which it is located.

The joint that connects superior plates 20a, 20b and inferior plates 30a, 30b can take many forms. In the embodiment shown in FIGS. 1-5, the mechanism is a pair of channels 40a, 40b formed in the inferior portions of superior plates 20a and 20b. A single channel 40a is formed in the inferior portion of superior plate 20a and a single channel 40b is formed in the inferior portion of superior plate 20b. Each channel 40a and 40b is sized to allow a superior portion of inferior plates 30a, 30b to extend into channels 40a, 40b respectively. Channels 40a, 40b extend generally longitudinally in the inferior portions of superior plates 20a and 20b respectively. This allows relative linear motion between superior plate 20a and inferior plate 30a and between superior plate 20b and inferior plate 30b. Alternatively, channels 40a' and 40b' may extend in a curvilinear direction, see e.g. FIG. 5, to allow more complex motion between superior plates 20a', 20b' and inferior plates 30a', 30b' respectively. Where channels 40a' and 40b' are curvilinear, the superior portions of inferior plates 30a' and 30b' have a curvilinear orientation as well, to match the profile of channels 40a' and 40b' and allow relative motion between inferior plates 30a' and 30b' and superior plates 20a' and 20b'. The radii of curvature for channels 40a' and 40b', as well as for the superior portions of inferior plates 30a' and 30b', should be chosen to allow for normal biomechanical movement between adjacent vertebrae. Thus, interspinous process device 100' shown in FIG. 5 allows more natural pivoting of the adjacent vertebrae when the spine is in flexion. A suitable lubricious coating may be included along the walls of the channels and/or along the superior portions of the inferior plates to reduce fretting and wear of these parts.

Channels 40a and 40b are defined by end walls 41a, 41b and a plurality of side walls. When the spine is in extension, interspinous process device 100 collapses by allowing the superior portions of inferior plates 30a and 30b to move completely into channels 40a and 40b respectively. End walls 41a and 41b act as a stop for the superior ends of the superior portions of inferior plates 30a and 30b, which are thus prevented from moving any farther superiorly along channels 40a and 40b. When the superior ends of the superior portions of inferior plates 30a and 30b are in contact with end walls 41a and 41b respectively, interspinous process device 100 is in its fully collapsed position. When interspinous process device 100 is in this position, the adjacent vertebrae on which interspinous process device 100 is affixed are held apart a sufficient amount to prevent compression of the relevant spinal nerves and provide pain relief for the patient. Thus, with interspinous process device 100, no spacer needs to be used to maintain decompression. However, if desired, spacer 60 can be used to act as a secondary stop that limits spinal extension and thus defines a minimum distance between the adjacent vertebrae. This ensures appropriate decompression for effective pain relief. In addition, spacer 60 alleviates some stress imposed on the adjacent spinous processes by the spikes 50 that are embedded therein by taking up some of the load on interspinous process device 100 when the spine is in extension.

The height of channels 40a and 40b and the length of the superior ends of inferior plates 30a and 30b that are disposed in channels 40a and 40b respectively are selected such that inferior plates 30a and 30b can not be completely withdrawn from channels 40a and 40b when the spine is in flexion. In other words, when the spine is in flexion and interspinous process device 100 is in its fully extended position, at least some part of the superior portions of inferior plates 30a and 30b are still disposed in channels 40a and 40b respectively. This maintains the integrity of interspinous process device 100.

It is to be understood that although the foregoing discussion discloses that the channels are disposed in the inferior portions of the superior plates, the channels could alternatively be formed in the superior portions of the inferior plates with the inferior portions of the superior plates being sized so they can be disposed in such channels. In addition, even though these embodiments have a pair of channels, it is to be understood that interspinous process device 100 could include a single channel formed in one of the superior plates or one of the inferior plates.

Spikes 50 are designed to be embedded in the lateral surface of the spinous processes when superior plates 40a and 40b and inferior plates 30a and 30b are squeezed laterally toward each other during implantation. Spikes 50 may have a pointed or otherwise sharp tip to facilitate embedding spikes 50 in the bone of the spinous process. With spikes 50 embedded in the lateral surfaces of the spinous processes, interspinous process device 100 is affixed to the adjacent spinous processes in the desired location.

Interspinous process device 100 is implanted such that superior plates 20a and 20b are located along opposite sides of a superior spinous process with spikes 50, located on the interior surface of superior plates 20a and 20b, embedded in the superior spinous process. Similarly, inferior plates 30a and 30b are located along opposite sides of the adjacent inferior spinous process with spikes 50, located on the interior surface of inferior plates 30a and 30b, embedded in the inferior spinous process. The superior portions of inferior plates 30a and 30b are located in channels 40a and 40b of superior plates 20a and 20b respectively. The combination of spikes 50, which fix interspinous process device 100 in place, and end walls 41a and 41b limit the amount that interspinous process device 100 can collapse. Moreover, there is no hard spacer needed to provide decompression. This eliminates a hard surface on which the adjacent spinous processes rest that could concentrate stresses on osteoporotic bone of the spinous processes. The elimination of a spacer is a significant advantage over current interspinous process devices where the spacer portion of the implant is formed from a hard material. Where spacer 60 is included in the interspinous process device of this invention, it may be sized so its diameter is slightly smaller than the distracted space between adjacent spinous processes when interspinous process device 100 is implanted. This prevents point loading on the spinous processes but still allows the spacer to act as a secondary stop in case spikes 50 somehow become disengaged from the spinous processes.

Other joints that connect the superior plates and inferior plates are contemplated as well. For example, the inferior portion of superior plates 20*a*", 20*b*" and the superior portion of inferior plates 30*a*", 30*b*" may be connected to a universally directional capsule 200 that allows relative movement between superior plates 20*a*", 20*b*" and inferior plates 30*a*", 30*b*" in three planes. See FIGS. 6-9. Capsules 200 are preferably formed from a solid filled polymeric material and have a generally oval or round configuration. The durometer of the polymeric material may be selected to provide an optimal level of controlled motion. Alternatively, capsules 200 may be a closed oval nitinol strip. Superior plates 20*a*" and 20*b*" and inferior plates 30*a*" and 30*b*" may be connected to capsules 200 by insert molding where the polymeric material of capsules 200 is molded around a portion of the plates. In order to ensure that the plates do not become detached from capsules 200, the inferior ends of superior plates 20*a*" and 20*b*" and the superior ends of inferior plates 30*a*" and 30*b*" can be dovetailed or flanged to create an undercut. Other connection methods include bonding or stitching the plates to capsule 200.

Capsules 200 allow superior plates 20*a*", 20*b*" and inferior plates 30*a*", 30*b*" to move relative to each other thus allowing (i) spinal flexibility in flexion and extension, (ii) lateral bending of the spine, and (ii) axial rotation of the spine. In addition, capsule 200 provides some shock absorption when the spine is in extension. In other words, instead of allowing the inferior ends of superior plates 20*a*", 20*b*" to abut the superior ends of inferior plates 30*a*", 30*b*" to abruptly stop extension of the spine, capsule 200 may provide controlled movement when the inferior ends of superior plates 20*a*", 20*b*" and the superior ends of inferior plates 30*a*", 30*b*" move toward each other. This would thus prevent an abrupt shock to the spine during extension. This controlled motion also minimizes some of the stresses placed on the spinous processes by the spikes 50 embedded therein to fix interspinous process device 100" in place. Of course, the overall height of interspinous process device 100" with capsule 200 in its fully compressed condition determines the extent of decompression provided. Where capsule 200 is relatively stiff and non-compressible, interspinous process device 100" limits flexion and extension. Where capsule 200 is more compliant, greater flexion and extension is possible.

Figure 10:
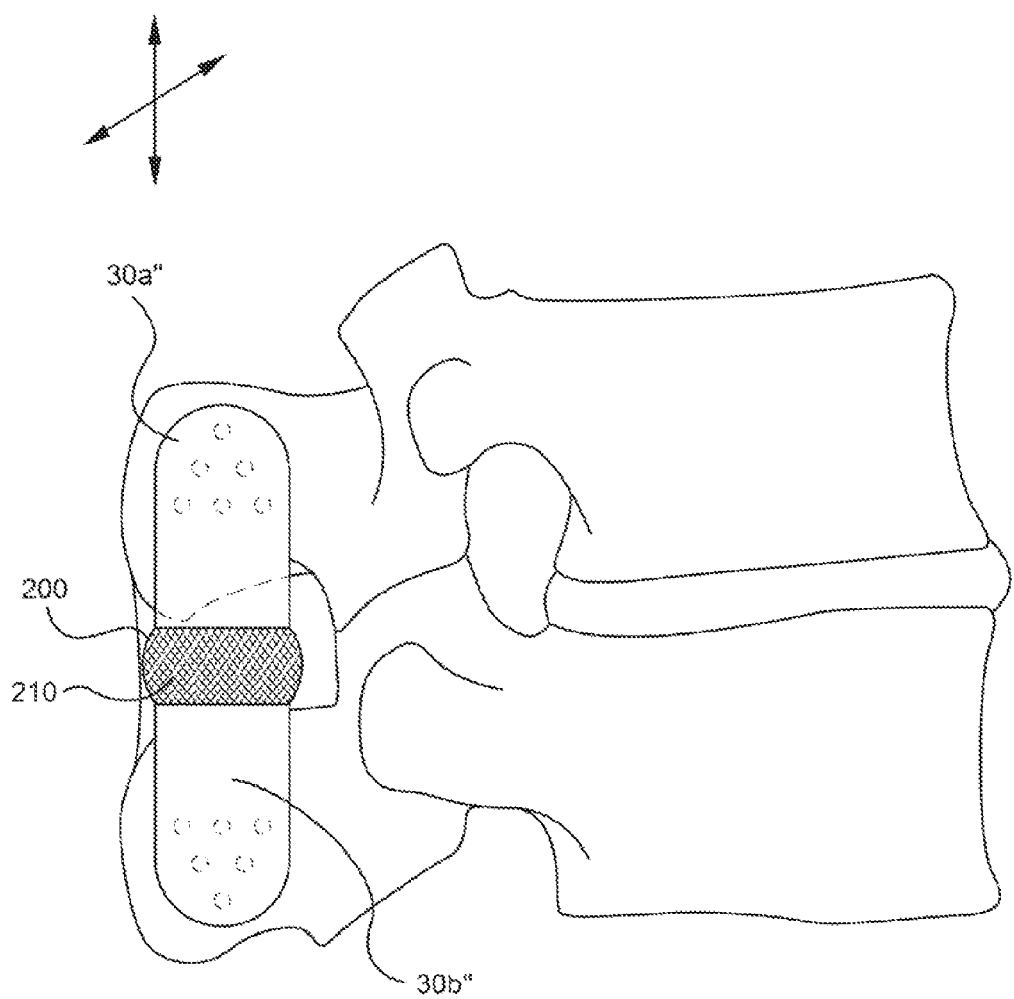
FIG. 10 is a side elevation view of another embodiment of an interspinous process device, which is similar to the device shown in FIG. 6, and a portion of a spine on which it is located.

As shown in FIG. 10, capsule 200 may include an outer net or woven material 210. Alternatively, capsule 200 may include an internal net or woven material, not shown. Such an internal or external net or woven material 210 will impart different characteristics for capsule 200. Moreover, by varying the tension of net 210, the relative motion between superior plates 20*a*", 20*b*" and inferior plates 30*a*", 30*b*" may be more precisely controlled. In other words, more tension on net 210 will result in capsule 200 being more resistant to motion since the increased tension will prevent significant stretching of the material. The material forming net 210 may include threads of nylon, polyester or metal. The openness of the weave of net 210 will also affect the tension of net 210 thereby imparting different characteristics on capsule 200 and affecting the relative motion between superior plates 20*a*", 20*b*" and inferior plates 30*a*", 30*b*" respectively.

Figure 11:
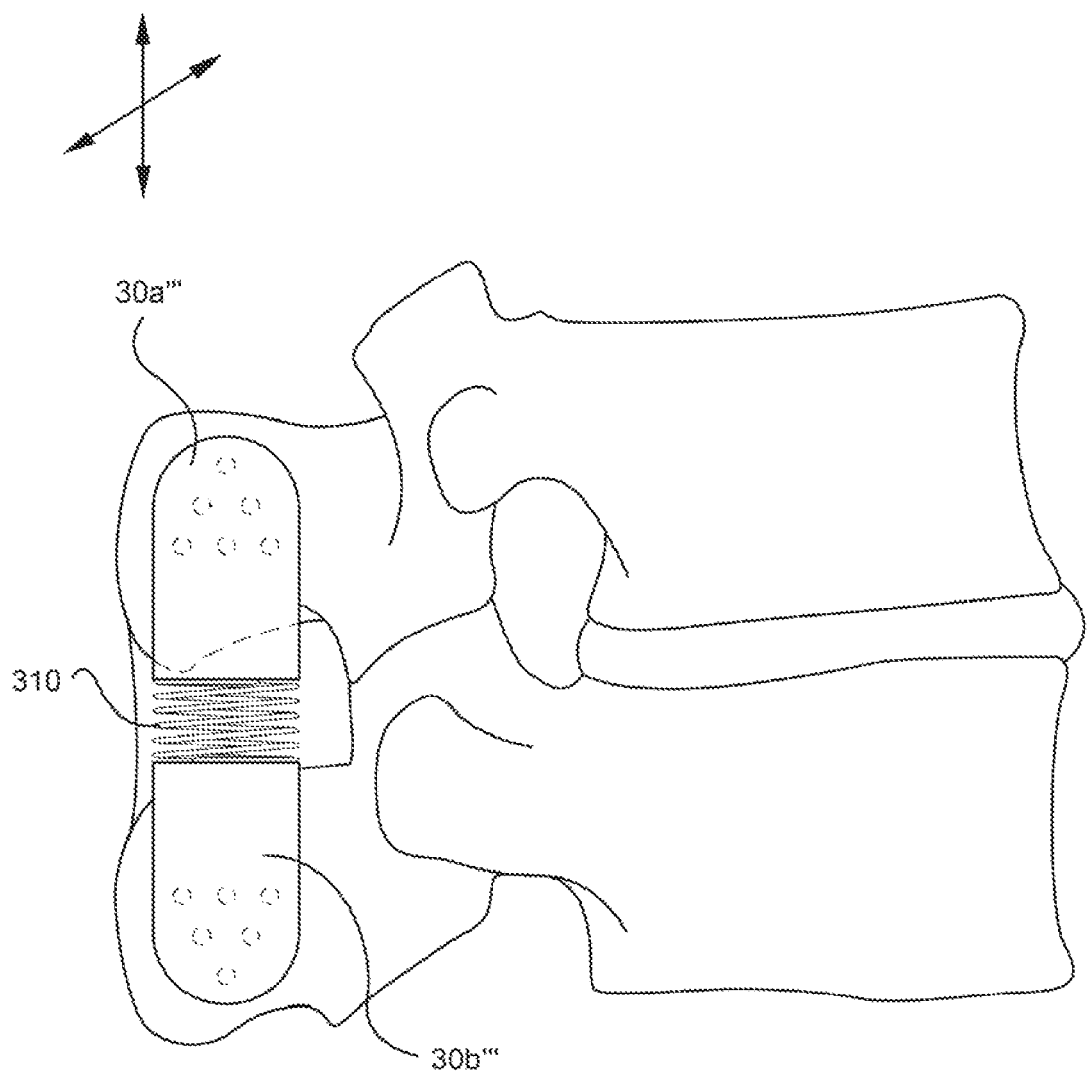
FIG. 11 is a side elevation view of yet another embodiment of an interspinous process device and a portion of a spine on which it is located.
Figure 12:
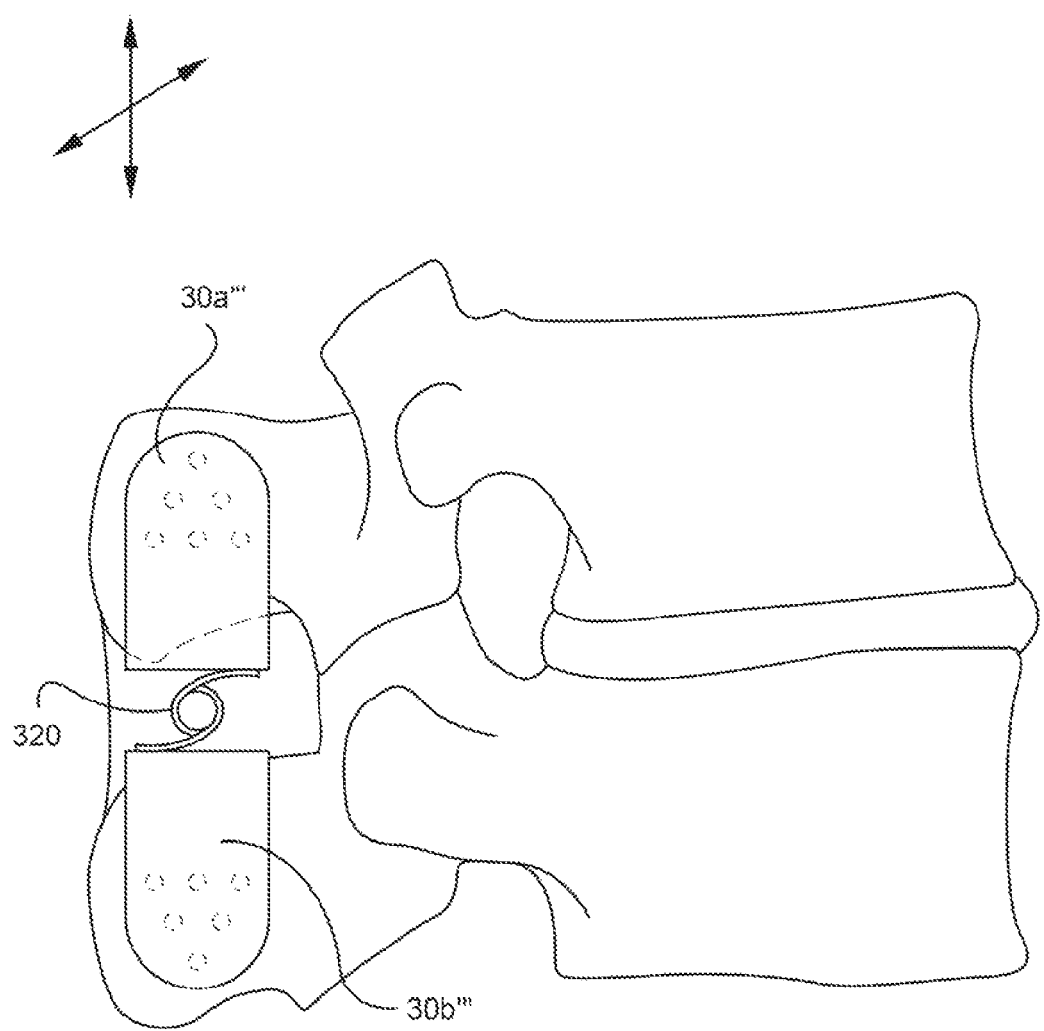
FIG. 12 is a side elevation view of still another embodiment of an interspinous process device and a portion of a spine on which it is located.

Another joint that connects the superior plates and the inferior plates includes a spring. For example, the inferior portion of superior plates 20*a*'", 20*b*'", and the superior portion of inferior plates 30*a*'", 30*b*'" may be connected to either a compression spring 310 or a torsion spring 320. The choice of a compression spring or a torsion spring is based on the relative movement desired for the interspinous process device. FIG. 11 shows the interspinous process device with compression spring 310, while FIG. 12 shows the use of torsion spring 320. The use of a spring to join superior plates 20*a*'", 20*b*'" to inferior plates 30*a*'", 30*b*'" respectively allows some motion of the spine in flexion and extension, as well as some lateral bending and axial rotation of the spine. The amount of such motion can be controlled by adjusting the spring constant of the spring and controlling the size of the spring. As with the embodiment of the interspinous process device shown in FIGS. 6-9, the springs used in this embodiment act as a shock absorber when the spine is in extension. Thus, instead of allowing the inferior ends of superior plates 20*a*'", 20*b*'" to abut the superior ends of inferior plates 30*a*'", 30*b*'" to abruptly stop extension of the spine, spring 310 and spring 320 may provide controlled movement when the inferior ends of superior plates 20*a*'", 20*b*'" and the superior ends of inferior plates 30*a*'", 30*b*'" move toward each other. This prevents an abrupt shock to the spine during extension. Of course, the overall height of the interspinous process device with spring 310 or spring 320 in the fully compressed condition determines the extent of decompression provided.

Figure 13:
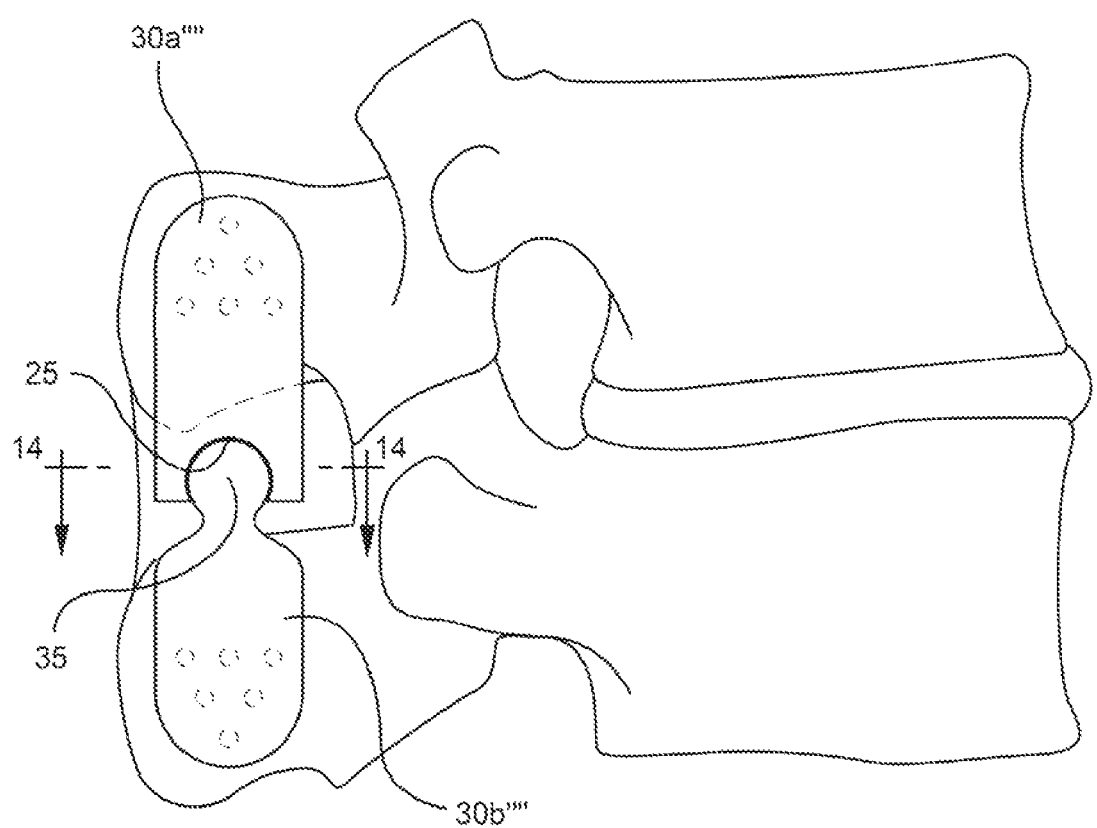
FIG. 13 is a side elevation view of a further embodiment of an interspinous process device and a portion of a spine on which it is located.
Figure 14:
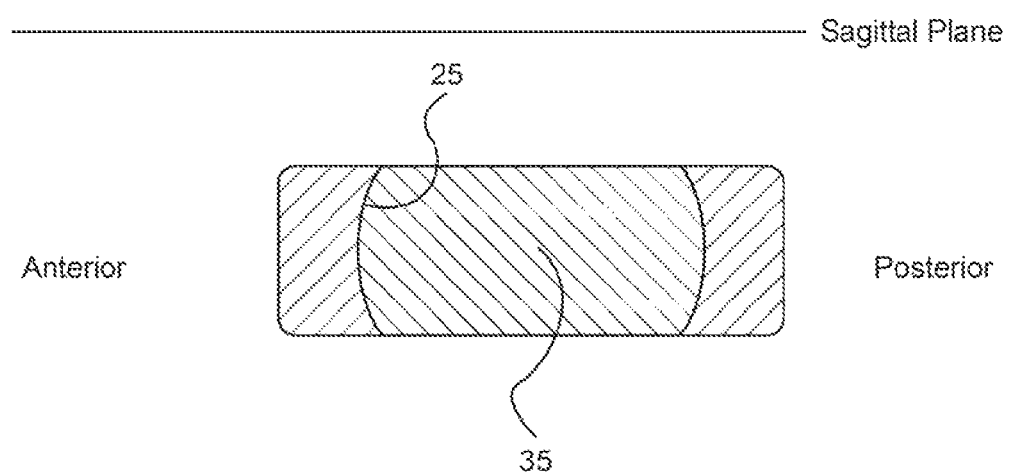
FIG. 14 is a cross sectional view of the interspinous process device shown in FIG. 13 taken along line 14-14 of FIG. 13.

Yet another joint that connects the superior plates and the inferior plates includes a ball joint. See FIG. 13. In this embodiment, the inferior ends of superior plates 20*a*"", 20*b*"" include a socket 25 and the superior ends of inferior plates 30*a*"", 30*b*"" include a ball 35 that fits within socket 25. This ball and socket configuration allows relative motion of superior plates 20*a*"", 20*b*"" with respect to inferior plates 30*a*"", 30*b*"" respectively. The extent of this relative motion can be controlled by providing corresponding planar surfaces on socket 25 and ball 35. See FIG. 14. For example if motion only along the sagittal plane is desired, the outer lateral surfaces of socket 25 and ball 35, as seen in FIG. 14, are flat, thus preventing rotation in the lateral direction while still allowing pivoting as the spine moves between flexion and extension. Of course, the inferior ends of the superior plates could include the ball and the superior ends of the inferior plates could include the socket.

The interspinous process device described herein can be constructed with various biocompatible materials such as, for example, titanium, titanium alloy, surgical steel, biocompatible metal alloys, stainless steel, Nitinol, plastic, polyetheretherketone (PEEK), carbon fiber, ultra-high molecular weight (UHMW) polyethylene, and other biocompatible polymeric materials. The material of the interspinous process device can have, for example, a compressive strength similar to or higher than that of bone. Alternatively, the interspinous process device may have a lower elastic modulus than bone.

While various embodiments of the interspinous process device have been described above, it should be understood that they have been presented by way of example only, and not limitation. Many modifications and variations will be apparent to the practitioner skilled in the art. The foregoing description of the interspinous process device is not intended to be exhaustive or to limit the scope of the invention. It is intended that the scope of the invention be defined by the following claims and their equivalents.

What is claimed is:

1. A device, comprising:
a first superior plate having a first inferior portion;
a second superior plate having a second inferior portion;
a first inferior plate having a first superior portion;
a second inferior plate having a second superior portion;
a first joint connecting the first inferior portion of the first superior plate to the first superior portion of the first inferior plate;
a second joint connecting the second inferior portion of the second superior plate to the second superior portion of the second inferior plate;
a plurality of spikes located along interior portions of the first superior plate and the second superior plate and along interior portions of the first inferior plate and the second inferior plate;
wherein the first and second joints are flexible;
wherein a first theoretical centerline intersects the first inferior portion of the first superior plate, the first superior portion of the first inferior plate, and the first joint;
wherein a second theoretical centerline intersects the second inferior portion of the second superior plate, the second superior portion of the inferior plate, and the second joint.

2. The device of claim 1 wherein the first and second superior plates are moveable in three planes relative to the first and second inferior plates respectively.

3. The device of claim 1 wherein the first and second joints are non-lockable.

4. The device of claim 1 further comprising a spacer disposed between the first superior plate and the second superior plate or between the first inferior plate and the second inferior plate.

5. The device of claim 1 wherein the first and second joints are molded around the first and second inferior portions of the first and second superior plates respectively and molded around the first and second superior portions of the first and second inferior plates respectively.

6. The device of claim 1 wherein the first and second inferior portions and the first and second superior portions are dovetailed direction.

7. The device of claim 1 wherein a first woven material is disposed over an outer surface of the first joint and a second woven material is disposed over an outer surface of the second joint.

8. The device of claim 1 wherein the first joint is a first spring and the second joint is a second spring.

9. The device of claim 8 wherein the first spring and the second spring are both compression springs.

10. The device of claim 8 wherein the first spring and the second spring are both torsion springs.

11. A device, comprising:
a first superior plate having a first inferior portion;
a second superior plate having a second inferior portion;
a first inferior plate having a first superior portion;
a second inferior plate having a second superior portion;
a first universally directional joint connecting the first inferior portion of the first superior plate to the first superior portion of the first inferior plate;
a second universally directional joint connecting the second inferior portion of the second superior plate to the second superior portion of the second inferior plate;
a plurality of spikes located along an interior portion of the first superior plate and the second superior plate and along the interior portions of the first inferior plate and the second inferior plate;
wherein the interior portion of the plates extends transverse to the inferior and superior portions of the respective plates;
wherein a first theoretical centerline intersects the first inferior portion of the first superior plate, the first superior portion of the first inferior plate, and the first joint;
wherein a second theoretical centerline intersects the second inferior portion of the second superior plate, the second superior portion of the second inferior plate, and the second joint.

12. The device of claim 11 wherein the first and second superior plates are moveable in three planes relative to the first and second inferior plates respectively.

13. The device of claim 11 wherein a first woven material disposed over an outer surface of the first joint and a second woven material disposed over an outer surface of the second joint.

14. The device of claim 11 wherein the first joint is a first spring and the second joint is a second spring.

15. The device of claim 14 wherein the first spring and the second spring are both compression springs.

16. The device of claim 14 wherein the first spring and the second spring are both torsion springs.

17. The device of claim 11 wherein the first joint is a first ball joint and the second joint is a second ball joint.

18. The device of claim 17 wherein the first ball joint includes a first ball have generally flat lateral sides and the second ball joint includes a second ball having generally flat lateral sides.

19. The device of claim 11 wherein the first and second joints are non-lockable.

20. The device of claim 11 wherein the first and second joints are molded around the first and second inferior portions of the first and second superior plates respectively and molded around the first and second superior portions of the first and second inferior plates respectively.

21. The device of claim 11 wherein the first and second inferior portions and the first and second superior portions are dovetailed.

* * * * *